US012239565B2

(12) United States Patent
Oliverio et al.

(10) Patent No.: US 12,239,565 B2
(45) Date of Patent: Mar. 4, 2025

(54) SAFE MOBILITY FOR PATIENTS

(71) Applicant: International Business Machines Corporation, Armonk, NY (US)

(72) Inventors: Stefania Oliverio, Rome (IT); Emilio De Angelis, Rome (IT); Giancarlo Delle Cese, Provincia di Frosinone (IT); Lorenzo Di Renzo, Rome (IT); Pia Toro, Rome (IT); Francesca Galeri, Fiumicino (IT); Chiara Conti, Rome (IT)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 916 days.

(21) Appl. No.: 15/980,029

(22) Filed: May 15, 2018

(65) Prior Publication Data
US 2019/0350742 A1  Nov. 21, 2019

(51) Int. Cl.
*A61F 5/37* (2006.01)
*A61B 5/00* (2006.01)
*G16H 40/63* (2018.01)

(52) U.S. Cl.
CPC .......... *A61F 5/3769* (2013.01); *A61B 5/0077* (2013.01); *A61F 5/3715* (2013.01);
(Continued)

(58) Field of Classification Search
CPC ........ A61F 5/37; A61F 5/3761; A61F 5/3715; A61F 5/3769; A61F 5/3723;
(Continued)

(56) References Cited

U.S. PATENT DOCUMENTS

| | | | |
|---|---|---|---|
| 8,448,606 B2 * | 5/2013 | Yackley | A01K 27/004 |
| | | | 119/796 |
| 8,833,310 B2 * | 9/2014 | Konigsberg | A01K 27/003 |
| | | | 119/770 |

(Continued)

FOREIGN PATENT DOCUMENTS

| | | |
|---|---|---|
| CN | 203458510 U | 3/2014 |
| WO | WO2017112651 A1 | 6/2017 |

OTHER PUBLICATIONS

L. Collins, et al "*Restraining Devices for Patients in Acute and Long-Term Care Facilities*" American Family Physician, 254-256, 79(4), Feb. 2009.

(Continued)

*Primary Examiner* — Alireza Nia
*Assistant Examiner* — Daniel A Miller
(74) *Attorney, Agent, or Firm* — Edward Wixted, Esq.; Heslin Rothenberg Farley & Mesiti P.C.; George S. Blasiak, Esq.

(57) ABSTRACT

Methods, computer program products, and systems are presented. The methods, computer program products, and systems can include, for instance: detecting, by machine logic, an event in a patient environment, wherein the event includes a body part of a patient moving to a location within a threshold distance of a point of interest, the point of interest being a location in the patient environment which if subject to contact by the body part poses risk to the patient; determining, by machine logic, one or more action to perform to control movement of the body part in response to the detecting the event in the patient environment; performing the one or more action to control movement of the body part in response to the detecting the event in the patient environment.

6 Claims, 12 Drawing Sheets

(52) U.S. Cl.
CPC .......... *A61F 5/3723* (2013.01); *G16H 40/63* (2018.01); *A61B 2562/0257* (2013.01)

(58) Field of Classification Search
CPC ...... A61F 5/3792; G61H 40/60; G61H 40/63; G61H 40/67; A61B 5/0077; A61B 2562/0257; A01K 15/02; A01K 15/04; A01K 27/003; A01K 27/004; E05B 73/00; E05B 73/0011; E05B 75/00; G06K 9/00; G06K 9/00771; G06K 9/46; G06V 20/00; G06V 20/52; G06V 20/44; G06V 40/103; G06V 40/28; G06V 40/23; G06V 40/20; G06V 10/235; G06V 10/25; G06V 10/945; G06F 3/00; G06F 3/048; G16H 50/20
USPC .................. 128/878, 879; 119/721
See application file for complete search history.

(56) References Cited

U.S. PATENT DOCUMENTS

| | | | |
|---|---|---|---|
| 8,851,019 B2* | 10/2014 | Jesurum | A01K 15/029 119/721 |
| 9,970,218 B1* | 5/2018 | Reed | B65H 75/4484 |
| 2005/0193782 A1* | 9/2005 | Beane | E05B 75/00 70/16 |
| 2006/0272366 A1* | 12/2006 | Kim | E05B 75/00 70/16 |
| 2013/0000653 A1 | 1/2013 | Vanderpool | |
| 2014/0026899 A1 | 1/2014 | Giese et al. | |
| 2015/0013690 A1* | 1/2015 | Dufek | A61F 5/3761 128/879 |
| 2015/0020750 A1 | 1/2015 | Jesurum | |
| 2016/0267327 A1* | 9/2016 | Franz | A61B 5/0077 |
| 2017/0091562 A1* | 3/2017 | Kusens | G06V 10/28 |
| 2017/0231531 A1* | 8/2017 | Heinrich | A61B 5/1128 600/476 |
| 2019/0104999 A1* | 4/2019 | De Haan | A61B 5/7264 |

OTHER PUBLICATIONS

Unkown "*Patient Restraints, Straight Jacket, Bed Restraints, Hospital Restraints, Leather Cuffs*" www.rehabmart.com/category/patient_restraints.htm, accessed Dec. 30, 2017.

* cited by examiner

SAFE MOBILITY FOR PATIENTS

BACKGROUND

Restraining devices are used in hospitals and other healthcare facilities to restrain patient movement. A restraining device can restrain a patient's movement and cannot be easily removed by a patient. Restraining devices are available in a variety of different form factors, e.g. a vest, a wrist restraint, geriatric chairs, and geriatric beds. Restraining devices may be used for a variety for purposes, e.g. to prevent falls, disruption of therapy, or wandering by a patient. Restraining devices have been used in hospitals and other healthcare facilities to attempt to control unpredictable behavior of patients. Restraining devices have also been used in surgical procedures, e.g. to properly orient the patient for surgery.

Data structures have been employed for improving operation of computer system. A data structure refers to an organization of data in a computer environment for improved computer system operation. Data structure types include containers, lists, stacks, queues, tables and graphs. Data structures have been employed for improved computer system operation e.g. in terms of algorithm efficiency, memory usage efficiency, maintainability, and reliability.

Artificial intelligence (AI) refers to intelligence exhibited by machines. Artificial intelligence (AI) research includes search and mathematical optimization, neural networks and probability. Artificial intelligence (AI) solutions involve features derived from research in a variety of different science and technology disciplines ranging from computer science, mathematics, psychology, linguistics, statistics, and neuroscience. Machine learning has been described as the field of study that gives computers the ability to learn without being explicitly programmed.

SUMMARY

Shortcomings of the prior art are overcome, and additional advantages are provided, through the provision, in one aspect, of a method. The method can include, for example: detecting, by machine logic, an event in a patient environment, wherein the event includes a body part of a patient moving to a location within a threshold distance of a point of interest, the point of interest being a location in the patient environment which if subject to contact by the body part poses risk to the patient; determining, by machine logic, one or more action to perform to control movement of the body part in response to the detecting the event in the patient environment; performing the one or more action to control movement of the body part in response to the detecting the event in the patient environment.

In another aspect, a computer program product can be provided. The computer program product can include a computer readable storage medium readable by one or more processing circuit and storing instructions for execution by one or more processor for performing a method. The method can include, for example: detecting, by machine logic, an event in a patient environment, wherein the event includes a body part of a patient moving to a location within a threshold distance of a point of interest, the point of interest being a location in the patient environment which if subject to contact by the body part poses risk to the patient; determining, by machine logic, one or more action to perform to control movement of the body part in response to the detecting the event in the patient environment; performing the one or more action to control movement of the body part in response to the detecting the event in the patient environment.

In a further aspect, a system can be provided. The system can include, for example a memory. In addition, the system can include one or more processor in communication with the memory. Further, the system can include program instructions executable by the one or more processor via the memory to perform a method. The method can include, for example: detecting, by machine logic, an event in a patient environment, wherein the event includes a body part of a patient moving to a location within a threshold distance of a point of interest, the point of interest being a location in the patient environment which if subject to contact by the body part poses risk to the patient; determining, by machine logic, one or more action to perform to control movement of the body part in response to the detecting the event in the patient environment; performing the one or more action to control movement of the body part in response to the detecting the event in the patient environment.

Additional features are realized through the techniques set forth herein. Other embodiments and aspects, including but not limited to methods, computer program product and system, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Figure 1:
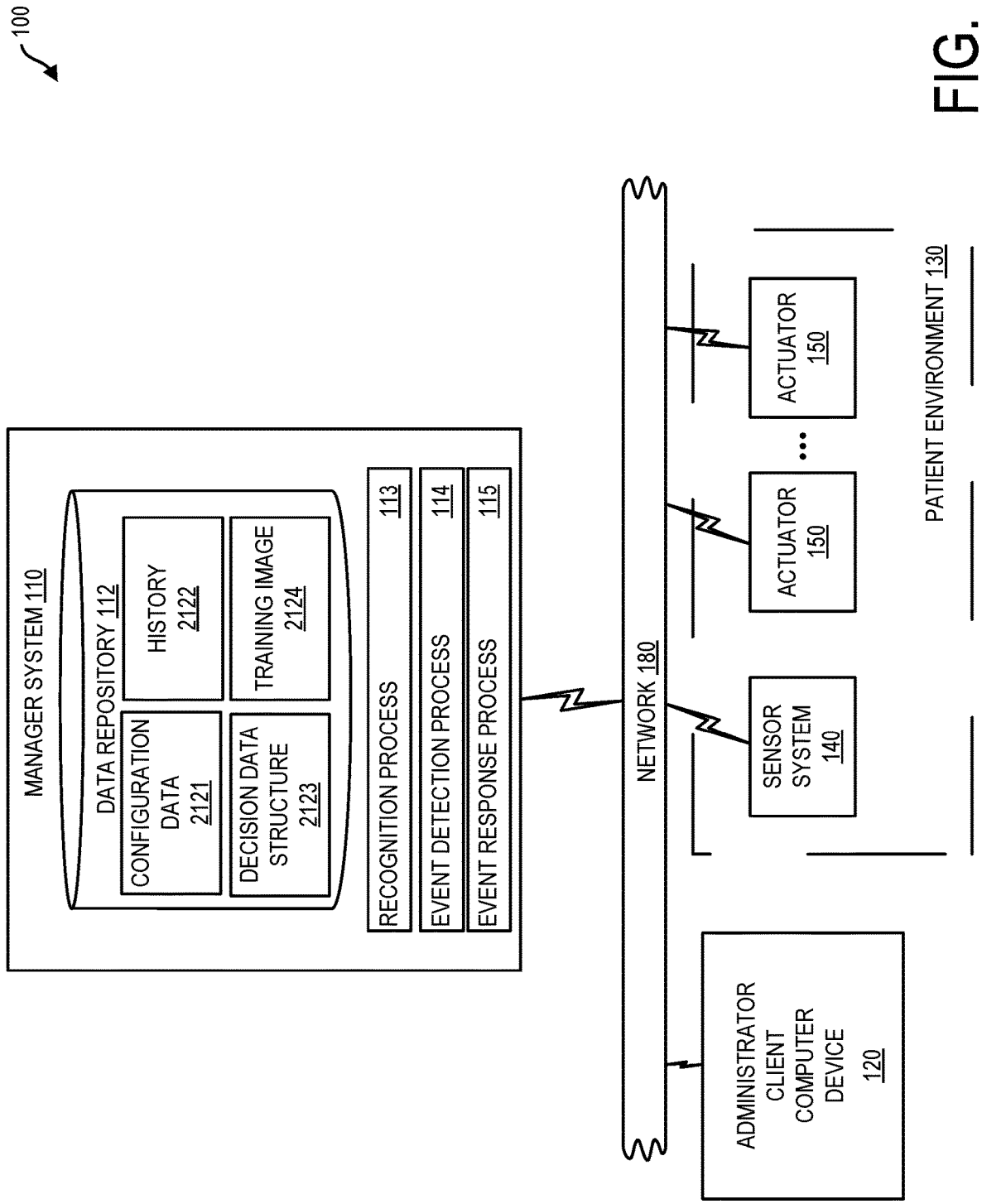
FIG. 1 is a block diagram illustrating a system having a manager system, a sensor system, and an actuator disposed for use with a patient environment according to one embodiment.

FIG. 1 is a block diagram of a system 100 for use in providing safe mobility to a patient receiving healthcare services according to one embodiment. System 100 can include manager system 110, administrator client computer device 120, and disposed within a patient environment 130 a sensor system 140, one or more actuator 150 for control of a patient's movement. Manager system 110, administrator client computer device 120, sensor system 140, and one or more actuator can be connected by a network 180. System 100 can include numerous devices which may be or include computing nodes as set forth herein. Network 180 may be a physical network and/or a virtual network. A physical network can be, for example, a physical telecommunications network connecting numerous computing nodes or systems, such as computer servers and computer clients. A virtual network can, for example, combine numerous physical networks or parts thereof into a logical virtual network. In another example, numerous virtual networks can be defined over a single physical network.

In one embodiment, manager system 110, administrator client computer device 120, sensor system 140, and one or more actuator 150 can be external to one another. In another embodiment one or more of manager system 110, administrator client computer device 120, sensor system 140, and/or one or more actuator 150 can be collocated with at least one of manager system 110, administrator client computer device 120, sensor system 140, and/or one or more actuator 150. Patient environment 130 in one embodiment can be provided within a healthcare facility such as a hospital or a home residence in which a patient is receiving healthcare services. According to one embodiment, patient environment 130 can include various objects such as a patient bed supporting a patient and an intravenous (IV) pole assembly for supporting an IV bag that defines an IV drip.

Embodiments herein recognize that features within a patient environment 130 can pose risk to a patient and in some scenarios, patients can actually cause injury to themselves. In some scenarios for example a patient may attempt, out of discomfort or as a result of a particular medical condition, to detach an IV drip currently feeding fluid to the patient or for example, attempt to remove an oxygen mask supplying oxygen to a patient. Embodiments herein recognize that possible approaches to dealing with the situation of a patient injuring himself or herself can actually pose additional risk to the patient's health. For example, embodiments herein recognize that restraining a patient's extremities without allowing movement of such extremities can actually pose greater danger to the patient. Embodiments herein recognize that a patient who attempts to move a body part such as an extremity but is restrained may actually experience significant stress as a result of the restraining, which may induce additional medical condition symptoms such as increased heartrate, blood pressure, and body temperature.

Embodiments herein recognize that medical staff may not always be able to give proper attention to the patients in hospital. Embodiments herein recognize that there are patients who may not be aware of their actions and could cause damage to themselves and to third parties. Embodiments herein recognize that post-operative patients and psychiatric patients frequently react with some emotional panic to restraints. Embodiments herein recognize that to avoid emotional problems, it is desirable to use a restraint that does not present to a patient as a restraint. Embodiments herein recognize that it can be advantageous to restrain only some movements of a patient but the patient should be left free to move in general. Embodiments herein recognize that drawbacks exist with existing approaches in that existing approaches in one aspect do not distinguish between dangerous and harmless movement, and the result is that the patient may be totally immobilized or left as is.

Embodiments herein can include features for facilitating safe mobility to patients. According to aspects herein features can facilitate free movement of a patient's extremities e.g. an area of a hand or foot unless an event is detected indicative of the patient's movement posing risk to himself or herself and then one or more action can be performed to alleviate the risk posing action.

Manager system 110 can include data repository 112 for storing data that supports various processes run by manager system 110 for providing safe mobility to a patient 190. Manager system 110 can run for example, recognition process 113, event detection process 114, and event response process 115.

Data repository 112 can include configuration data area 2121 for storing configuration data, history area 2122 for storing history data, decision data structure area 2123, and training image area 2124.

Configuration data stored in configuration data area 2121 can include for example, administrator user defined configuration data defined by an administrator user, using an administrator user interface. Configuration data can include data defining, e.g. one or more mobility point and one or more point of interest. A mobility point in one embodiment can be a point on a patient 190 that is subject to movement by the patient 190. A mobility point can be for example, an extremity of a patient 190 such as a hand or a foot, or another body part which the patient 190 can move such as the patient's torso or head. The point of interest can be for example, a location in a patient environment 130 that can pose risk to a patient 190 if reached by a defined mobility point. One example of a point of interest that can be configured and specified in configuration data of configuration data area 2121 is an IV drip point of interest. Another example of a point of interest is an oxygen mask. Points of interest can also include for example endotracheal tubes, intracatheters, patient bandages, and medical equipment, and patient environment 130 doorways.

Configuration data of configuration data area 2121 can include configuration data that defines events that can be recognized by manager system 110. An example of an event can be that a patient 190 moved a mobility point to a location within a threshold distance from a point of interest, e.g. has moved a hand too close to an IV drip interface. Configuration data of configuration data area 2121 can include configuration data defining a response provided by manager system 110 in response to an event being detected, such as a patient 190 mobility point being moved within a proximity threshold to a point of interest. For some points of interest, and/or mobility points for example, a first response can be defined and for a second point of interest and/or mobility point, a second response can be defined. Responses can be differentiated, e.g. in terms of speed at which a mobility point is caused to be moved away from a point of interest and/or lock release timeouts as are explained further herein.

History area 2122 can store data, e.g. on prior configurations used by manager system 110. Using system 100 for example, an administrator user can establish different configurations for different users, e.g. a first configuration for a first patient and a second configuration for a second patient. If system 100 is reused for return patient, for example, an administrator user can recall from history area 2122 to establish based configuration parameters in setting up system 100 which base configuration parameters can be adjusted. In one embodiment, history area 2122 can also store performance data specifying performance parameters for a system 100 during past configurations and uses. Performance parameters can include, e.g. patient diagnostic parameters, e.g. heartrate, blood pressure, temperature, and the like during use. Accordingly, manager system 110 in some embodiments can use such past parameters to provide prompts to an administrator user on an administrator user interface 500 as set forth herein. A prompt can advise an administrator user for example to avoid past parameters if the configuration biometric data indicates that the patient experienced discomfort, or suggest certain elements to incorporate from successfully performing past configurations.

Decision data structure area 2123 can include for example a decision data structure that cognitively maps events to one or more action that can be associated to the events. The events like the one or more action can be configured using configuration data that can be defined by an administrator user using an administrator user interface 500 displayed on administrator client computer device 120.

Training image area 2124 can include training images used for facilitating processing of image data by manager system 110 for recognition of objects. For example, an administrator user can specify objects as points of interest or mobility points as set forth herein and images of such objects can be uploaded to training image area 2124 to improve the ability of manager system 110 to recognize such objects.

Manager system 110 can run recognition process 113, event detection process 114, and event response process 115 in accordance with configuration data stored in configuration data area 2121 according to one embodiment.

Manager system 110 can run recognition process 113 to recognize objects in patient environment 130. Manager system 110 can run recognition process 113 to process data obtained from sensor system 140 for the recognition of objects. In one embodiment, sensor system 140 can be provided by a camera system having one or more camera, and the camera can iteratively provide frames of image data which can be processed by manager system 110 running recognition process 113. Objects recognized by manager system 110 running recognition process 113 can include, e.g. mobility points and points of interest as set forth herein, e.g. extremities of a patient 190 defining a mobility point and an IV drip interface or an oxygen mask defining a point of interest.

Manager system 110 running recognition process 113 can include manager system 110 performing pattern recognition to recognize image data representations of specified points of interest and mobility points in a captured frame of image data. Pattern recognition systems can employ labeled training data which can be input into a pattern recognition system to provide supervised learning. Pattern recognition processes can employ, e.g. classification algorithms such as supervised algorithms predicting categorical labels, clustering algorithms, e.g. unsupervised algorithms predicting categorical labels, ensemble learning algorithms, general algorithms for predicting arbitrarily structure sets of labels, real value sequence labeling algorithms, regression algorithms, pattern recognition algorithms can employ various digital image processing techniques, e.g. for classification feature extraction, multiscale signal analysis, and projection. Digital image processing techniques can include use of digital image transformations, such as application of digital filters which are useful for performance of feature extraction for detection, e.g. of edges, corners, blobs, and ridges. Shape based digital image processing techniques can use, e.g. techniques involving blob extraction, template matching, or Hough transforms. Image data subject to processing by recognition process 113 can include, e.g. 2D image data and/or 3D point cloud image data.

Manager system 110 running event detection process 114 can detect for one or more event specified by configuration parameters stored in configuration data area 2121. A defined event can be, e.g. the event that a patient 190 has moved his or her body part to a distance that is within a threshold distance from a point of interest. Such event can indicate that the patient 190 is at risk of injuring himself or herself and can specifically indicate such events as the event that a patient 190 is attempting to disconnect himself or herself from an IV drip or is attempting to remove an oxygen mask.

Manager system 110 running event detection process 114 can include manager system 110 tracking coordinate locations of one or more defined mobility point and one or more point of interest. Manager system 110 running event detection process 114 can include manager system 110 processing a succession of frames of image data. The processing of each frame of image data can include identifying within each frame each defined mobility point and each defined point of interest, and determining a coordinate location of each such recognized mobility point and point of interest. Mobility point coordinate locations and/or point of interest coordinate locations can change from frame to frame in a succession of frames of image data, e.g. while a patient 190 moves one or more body part and/or a location of a point of interest such as an IV drip interface or oxygen mask changes.

With the processing of each frame, manager system 110 running event detection process 114 can examine coordinate location data for defined mobility points and points of interest to determine a set of distance parameters that specify distance of each mobility point to each point of interest. With the processing of each frame, manager system 110 running event detection process 114 can further compare such distance parameters to establish distance thresholds established for each mobility point and point of interest pair. Manager system 110 running event detection process 114 can raise a flag indicating that an event has occurred based on determining that a current distance between a mobility point and a point of interest is less than an established threshold distance. Based on an event flag being raised, manager system 110 can run an event response process 115 to respond to a detected event.

Manager system 110 running event response process 115 can activate one or more action in response to a detected event. For activating an action, manager system 110 can use a decision data structure of decision data structure area 2123 of data repository 112. A decision data structure of decision data structure area 2123 according to one embodiment can cognitively map depicted events to actions associated with such events. Actions that area specified within a such a decision data structure can be provisioned based on configuration data of configuration data area 2121. Embodiments herein recognize that a best response can vary depending, e.g. on the patient and/or on the event detected. For example, based on the occurrence of a first event the best course of action may be to slowly urge movement of a patient's body part from a risk location. Based on the occurrence of a second event, a best course of action may be to quickly urge movement of a patient's body part from a risk location.

Manager system 110 running event detection process 114 can determine coordinates of defined mobility points and points of interest. In the case image data being processed is 3D image data, image data representing a mobility point or a point of interest can inherently encode 3D location coordinates, e.g. having voxels representing biometric regions at certain X, Y, and Z coordinate locations. In the case manager system 110 running event detection process 114 processes 2D image data, 3D image data, and X, Y, and Z coordinate locations for identified mobility points and/or points of interest can be determined using, e.g. camera coordinates camera angle and dimensions in known items within patient environment 130 being subject to camera imaging.

Sensor system 140 disposed within patient environment 130 according to one embodiment can include a camera system including one or more camera. Sensor system 140 provided by a camera system in one embodiment can provide 2D image data and in one embodiment can provide 3D point cloud image data. Sensor system 140 can include one or more camera such a camera having an image sensor chip including an array of light sensitive pixels and an associated imaging lens. Sensor system 140 to provide 3D point cloud image data can include in one embodiment a 3D camera capable of providing 3D point cloud image data. In one embodiment a 3D camera of sensor system 140 can be provided by a light detection and ranging (LIDAR) camera. In one embodiment a LIDAR camera can measure a distance to a target by illuminating the target with pulse laser light and measuring reflected pulses with a sensor. Differences in laser return times and wavelengths can be used to make digital 3D point cloud representations of the target. In some embodiments, sensor system 140 can be configured to provide 3D image data with use of a plurality of 2D cameras.

One or more actuator 150 within patient environment 130 can be provided by motor based actuator. In one embodiment one or more actuator 150 can be operated to control a rate at which a location of a patient's body part has changed.

Figure 2A:
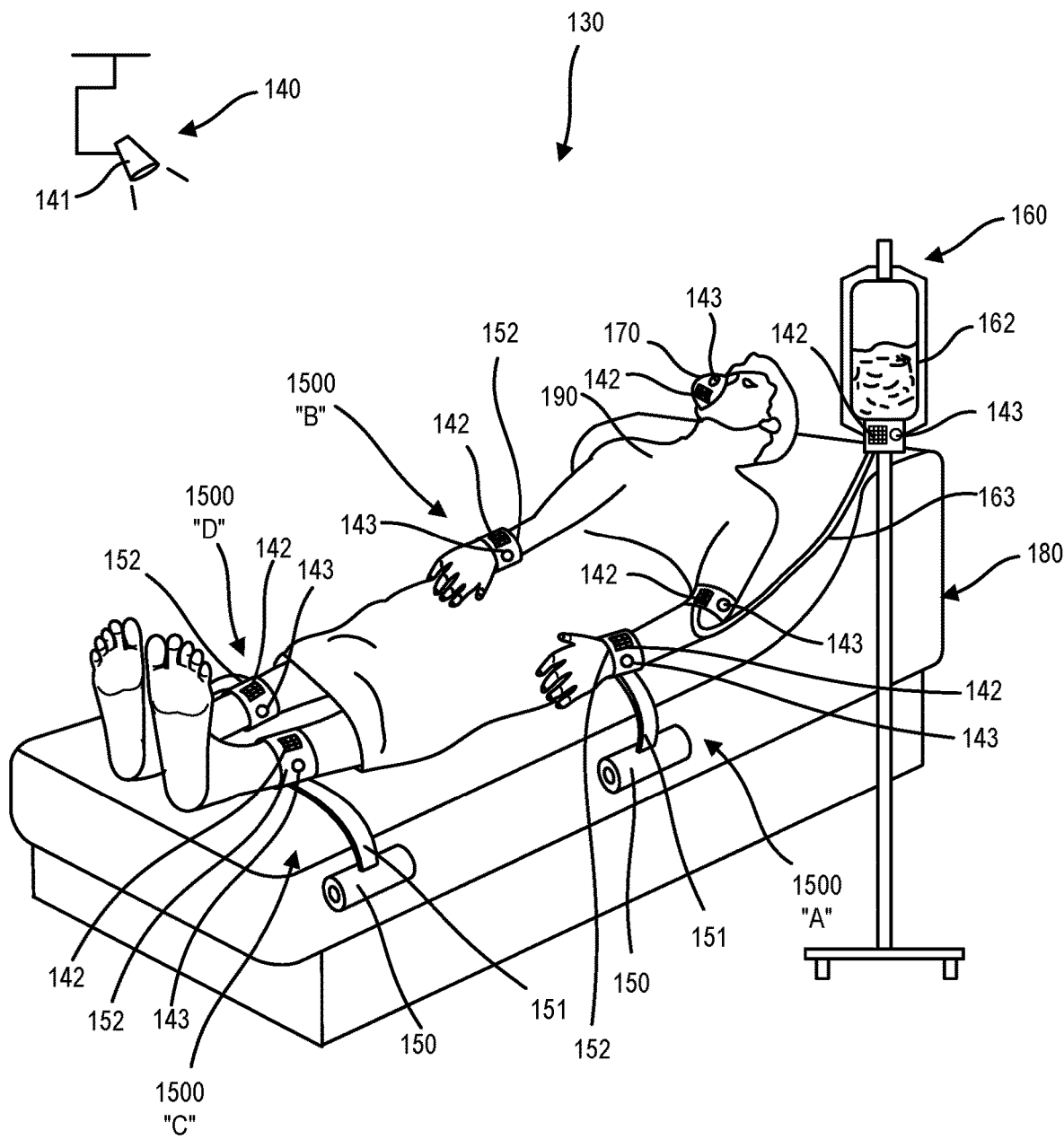
FIG. 2A is a perspective view of a patient environment according to one embodiment.

FIG. 2A is a perspective view of patient environment 130 set forth in block diagram form in FIG. 1. Patient environment 130 can include sensor system 140, provided, in the example shown, by a camera for capturing frames of image data representing patient 190 and other objects such as a bed as shown, IV pole assembly 160 supporting IV bag 162 that provides an IV drip to patient 190. Patient environment 130 can also include one or more actuator 150 that can be provided as part of an actuator assembly. One or more actuator 150 can be provided to control movement of a body part of patient 190.

According to the embodiment shown in FIG. 2A there can be provided by four actuator assemblies 1500, e.g. at locations "A", "B", "C", and "D" as depicted in FIG. 2A. Each actuator assembly 1500 can include an actuator 150 that can be provided by a rotary actuator. Actuator 150 can be actuated to roll and unroll an associated band 151. Further there can be provided for each actuator assembly 1500, a cuff 152 disposed on a band 151. According to FIG. 2A actuator 150 can be actuated to roll and unroll (wind and unwind) band 151 attached to cuff 152. Each actuator assembly 1500 can have a locked state and an unlocked state. In a locked state, a patient 190 cannot increase the length of band 151 extending outwardly from actuator 150. In an unlocked state a patient 190 can extend a length of band 151 extending from actuator 150.

Each actuator 150 as set forth in FIG. 2A can be provided by an electric retractor that includes a rotatable spool attached to a retractor frame. Band 151 can be wound on the spool. In normal usage the spool can be controlled by a coil, allowing extensions and rewindings of band 151 when patient 190 brings his or her body part back to actuator 150. Depending on triggers, actuator 150 can block the extension of band 151 or rewind band 151 by running the actuator 150 including electric motor that can be disposed within the spool. Actuator 150 can have associated computing nodes as described further herein. In some embodiments computing node for an actuator 150 can include a microcontroller. Actuators 150 can include network adapters, e.g. wireline or wireless network adapters that provide bidirectional communication with manager system 110 via network 180.

Sensor system 140 as depicted in FIG. 2A can be provided be a ceiling mounted camera in one embodiment as depicted in FIG. 2A. However alternative arrangements can be provided, e.g. multiple cameras and/or drone mounted cameras that can be mounted to a drone to make any camera angle in relation to a patient 190 within a patient environment 130, can be provided. With a drone mounted camera, a viewing angle of the camera can be moved between locations over the course of use of system 100.

Figure 2B:
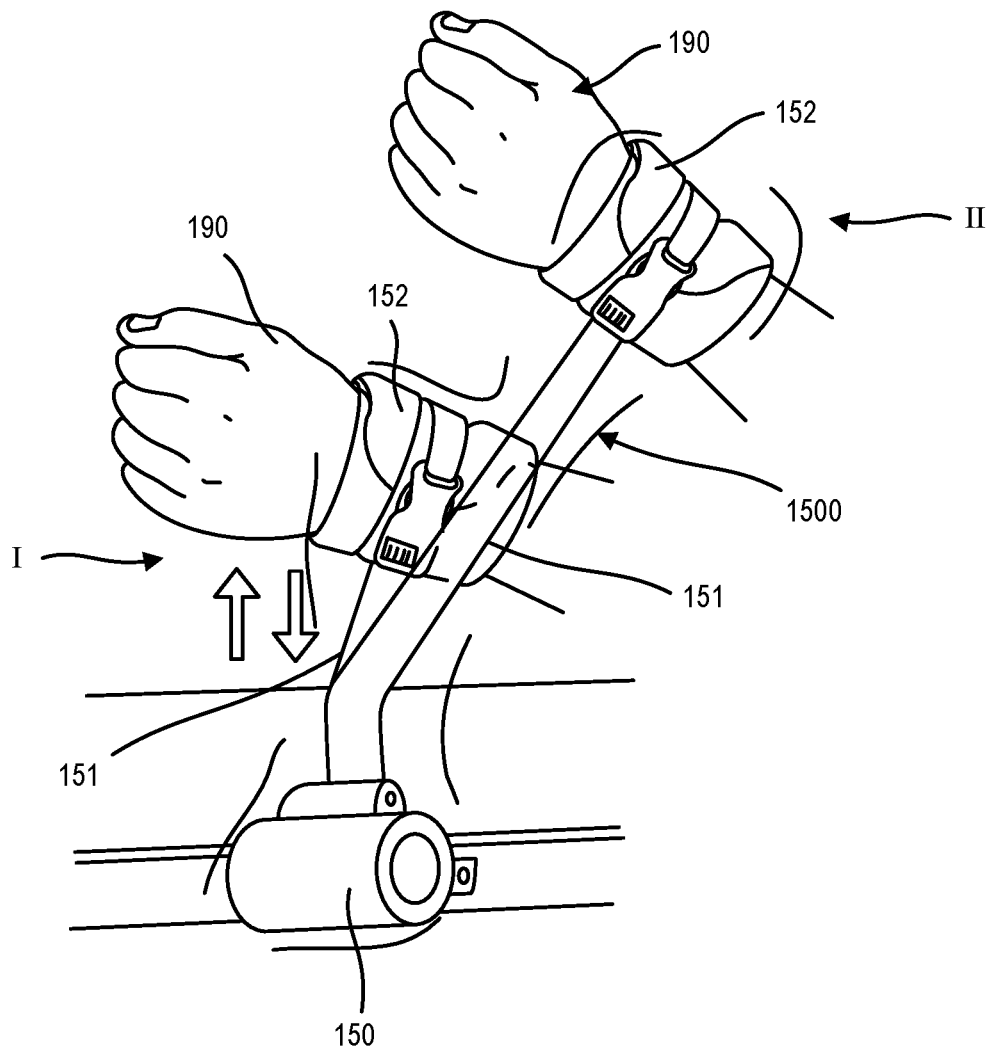
FIG. 2B is a schematic perspective view depicting operation of an actuator assembly according to one embodiment.

FIG. 2B further illustrates operation of an actuator assembly 1500 in a locked state and an unlocked state. In an unlocked state depicted by "I" the attempt of patient 190 to move his or her hand extremity upward is restrained by actuator 150, which by virtue of it being in a locked state restrains length of band 151 that can extend outwardly from an actuator 150 and therefore restrains the location of the extremity to a location closely spaced to actuator 150. The spacing distances being defined by the fixed distance of band 151 extending from actuator 150. In an unlocked state depicted by "II" a patient 190 is able to move his or her extremity freely to any location spaced from actuator 150 until band 151 is fully unwound from the spool provided as part of actuator 150. Until the time that band 151 is fully unwound, band 151 unwinds from the spool to permit free movement of an extremity of patient 190, such as the patient's hand depicted in FIG. 2B. Actuator 150 as set forth in FIG. 2B can be provided by an electric retractor that includes a motorized rotatable spool attached to a retractor frame. Band 151 can be wound on the spool. In normal usage the spool can be controlled by a coil, allowing extensions and rewinding of band 151 when patient 190 brings his or her extremity back to actuator 150. The coil keeps a length of band 151 between a patient 190 and actuator 150 to a minimum, removing risk that loose or hanging portions of band 151 becoming entangled with interfering objects within patient environment 130.

Figure 3:
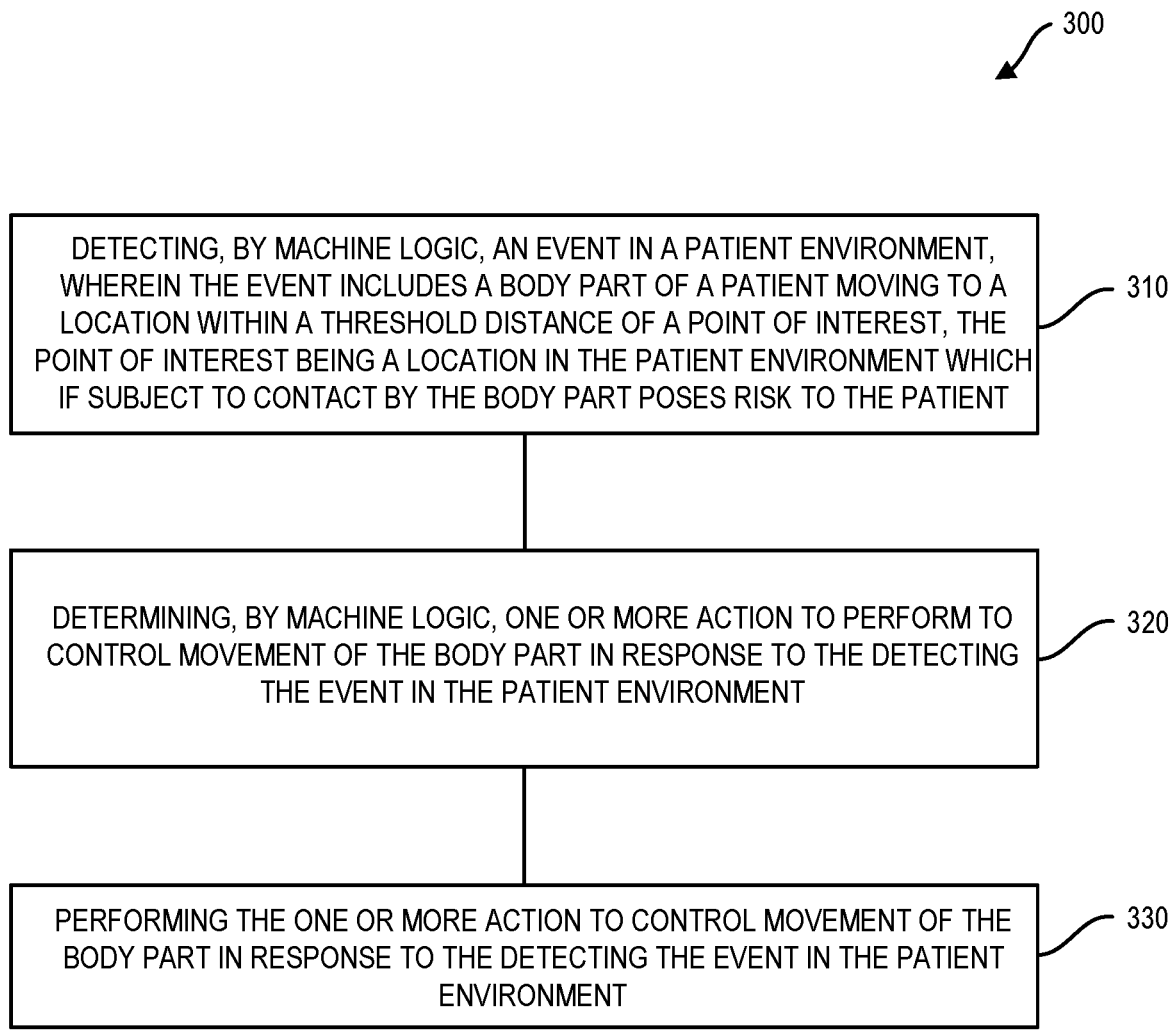
FIG. 3 is a flowchart depicting a method that can be performed by manager system according to one embodiment.

A method 300 for performance by manager system 110 is shown in FIG. 3. At block 310 manager system 110 can perform detecting, by machine logic, an event in a patient environment 130, wherein the event includes a body part of a patient moving to a location within a threshold distance of a point of interest, the point of interest being a location in the patient environment 130 which if subject to contact by the body part poses risk to the patient 190. At block 320 manager system 110 can perform determining, by machine logic, one or more action to perform to control movement of the body part in response to the detecting the event in the patient environment 130. At block 330 manager system 110 can perform performing the one or more action to control movement of the body part in response to the detecting the event in the patient environment 130.

Figure 4:
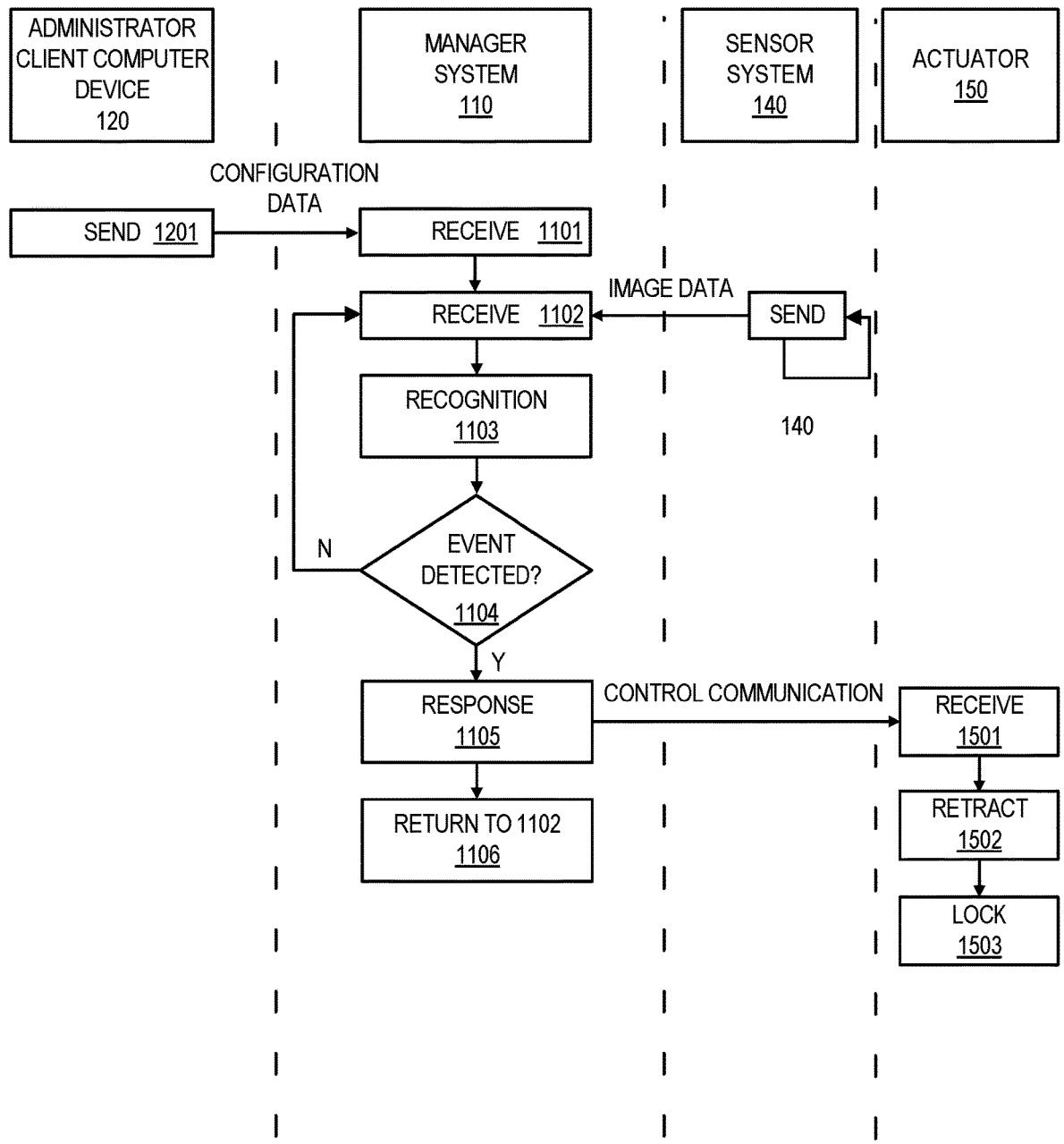
FIG. 4 is a flowchart depicting operation of a method that can be performed by a system according to one embodiment.

The flowchart of FIG. 4 depicts an example of method 300 as illustrated in FIG. 3. The flowchart of FIG. 4 depicts manager system 110 interoperating with administrator client computer device 120 and sensor system 140. At block 1201, administrator client computer device 120 can send configuration data for receipt by manager system 110 at block 1101. The configuration data sent can be administrator user defined configuration data define by an administrator user using an administrator user interface 500 as depicted in FIG. 5.

Figure 5:
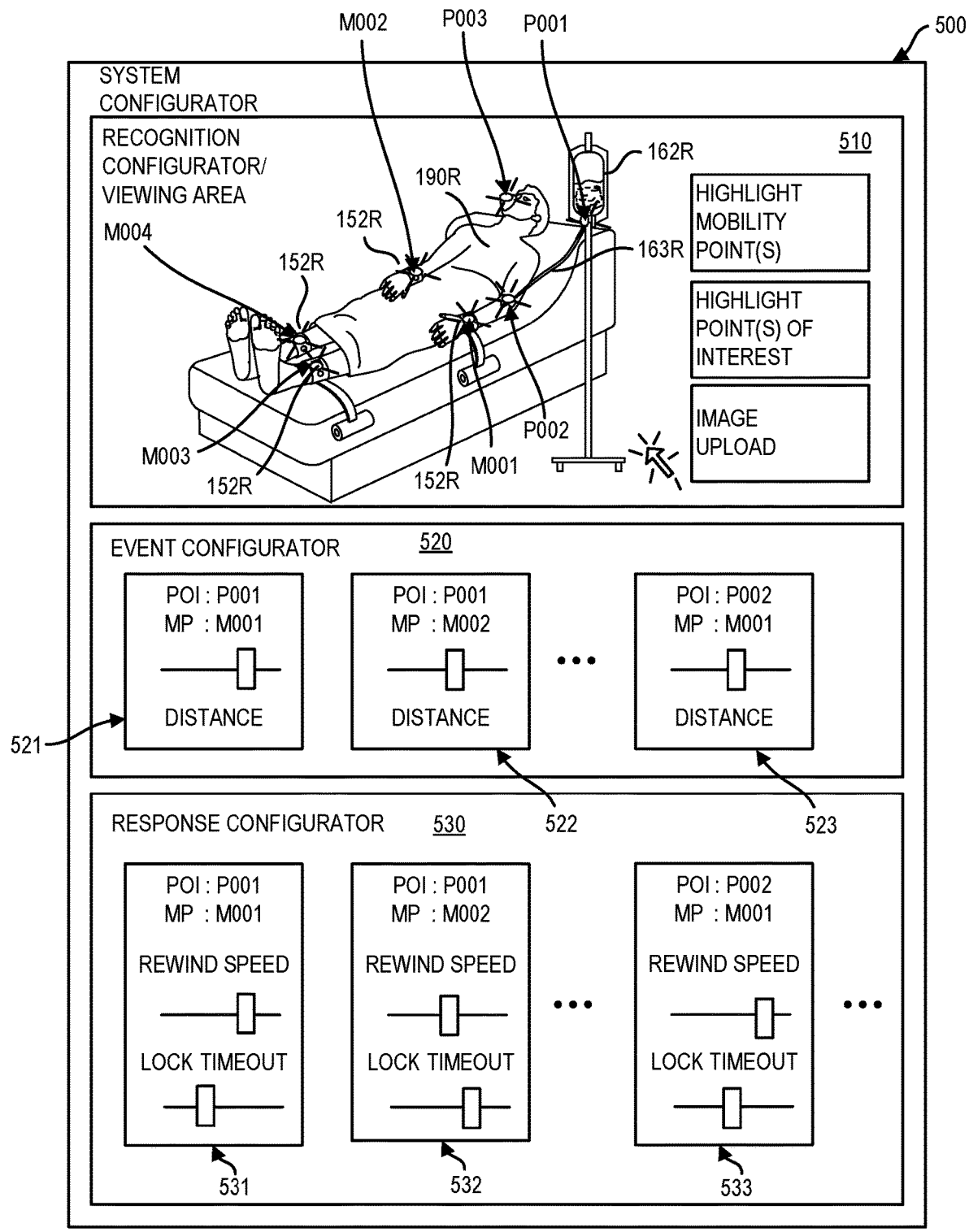
FIG. 5 depicts an administrator user interface that can be displayed on a display of an administrator client computer device according to one embodiment.

Using administrator user interface 500 as depicted in FIG. 5, an administrator user can establish various administrator user selections that configure system 100 for use in facilitating safe mobility by a patient 190 so that a patient 190 can freely move extremities for increased comfort and reduced stress with exceptions to free movement being guided in select instances, e.g. where system 100 detects that a patient 190 may cause harm to himself or herself.

IV bag 162 together with feed tube 163 defines an IV drip. The defined IV drip as first and second IV drip interfaces that define potential points of interest that might be specified by an administrator user using an administrator user interface 500. The first interface is the interface between IV bag 162 and feed tube 163, the second interface is the interface between feed tube 163 and patient 190.

Referring to area 510 of administrator user interface 500, area 510 can be displaying by default real time images of patient environment 130. System 100 can be configured further so that area 510 has a mode of operation permitting area 510 to display an image representation of patient environment 130 (FIG. 1). Administrator user interface 500 can be a displayed manually operated user interface, displayed on a display of administrator client computer device 120. Real time or still images displayed within area 510 can be based on image data obtained from one or more camera so that a field of view of the camera encompasses patient environment 130. The camera can be a camera of sensor system 140. The view angle can be, e.g. a top view angle which can be produced by the camera defining sensor system 140 depicted in FIG. 2A, in addition or alternatively the camera can provide a front perspective view angle, e.g. producing the view as depicted in FIG. 2A which can be produced by a camera of sensor system 140.

Using area 510 with a still image display mode activated an administrator user can specify mobility points and points of interest using the displayed image representing patient environment 130. Configurating can alternatively be performed by an administrator user interacting with a moving video image representation of a patient environment 130 being displayed. On activating the "highlight mobility point(s)" control within area 510, an administrator user interface 500 can display a series of prompts prompting an administrator user to define mobility points. An administrator user can be permitted to move a cursor about the displayed image and then "point and click" to designate a mobility point. For a displayed image corresponding to the view depicted in FIG. 2A for example administrator user might "point and click" to highlight each of the four cuff 152 of the four actuator assemblies 1500. In the described example depicted with reference to area 510, four cuff 152 can be selected as mobility points represented as mobility points M001, M002, M003, and M004 in area 510 of administrator user interface 500. On activating the "highlight point(s) of interest" control within area 510, an administrator user can be presented a series of prompts prompting an administrator user to define points of interest.

Referring to the perspective view of a patient area of FIG. 2A of patient environment 130, an administrator user may select first and second interfaces of the defined IV drip as points of interest. More specifically, a first interface between IV bag 162 and feed tube 163 can be defined as a point of interest. Also, an interface between feed tube 163 and patient 190 can be defined as a point of interest. Further, oxygen mask 170 can be defined as a point of interest. Representations 162R, 163R, 170R, 190R, 152R of IV bag 162, feed tube 163, oxygen mask 170, and cuff 152, respectively, together with representations of remaining features of patient environment 130 as set forth in FIG. 1A can be displayed on administrator user interface 500. Administrator user interface 500 can be configured so that an administrator user can specify the referenced features as points of interest using a displayed still image representation or moving image representation representing patient environment 130 displayed within area 510. By pointing and clicking corresponding representations of the described features, administrator user can specify the first and second IV drip interfaces as points of interest P001 and P002 respectively. An administrator user can specify oxygen mask represented by oxygen mask representation 170R as point of interest P003 within the representation of a patient environment 130 displayed within area 510.

Points of interest that can be specified by an administrator user using administrator user interface 500 can also include for example endotracheal tubes, intracatheters, patient bandages, and/or medical equipment, or a patient environment exit door. Mobility points that can be specified by an administrator user using administrator user interface 500 can also include for example a patient 190 head or torso. It can be advantageous to monitor for example to monitor a distance between a patient 190 torso and a patient door to monitor whether a patient is attempting to vacate a bed. For such monitoring a patient 190 exiting configured by an administrator user specifying a distance less than a patient bed to door distance so that a patient 190 attempting to exit can be detected as an event.

By actuation of image upload control 513 an administrator user can be presented a series of prompts prompting an administrator user to enter training images for uploading into training images area 2124 of data repository 112. For each specified mobility point and point of interest specifies using area 510 an administrator user can be prompted to enter training images so that manager system 110 running recognition process 113 has an improved ability to recognize a mobility point or point of interest. A prompt can include such prompt as depiction of a cropped image isolated to show the selected mobility point or point of interest with accompanying text such as "PLEASE UPLOAD ADDITIONAL IMAGES OF THE SELECTED FEATURE DEPICTED IN THIS CLIP." An administrator user can then use administrator client computer device 120 to upload the prompted four images.

In one embodiment, administrator client computer device 120 can be provided by a mobile computer device, e.g. a smartphone and system 100 can be provisioned with appropriate software so that an administrator user in response to a prompt for training images can move into patient environment 130 and use the mobile computer device defining administrator client computer device 120 to obtain close up high-resolution images of different angles of the prompted-for features. Manager system 110 can thus be trained to more accurately identify specified mobility points and points of interest.

Using area 520 of administrator user interface 500 an administrator user can define configuration parameters that specify events that can be detected by manager system 110. In one embodiment an event can be specified to occur when a patient 190 moves a body part to a distance with respect to a define point of interest that is less than a threshold distance. Using area 520 administrator user can specify such threshold distances for each possible point of interest and mobility point combination.

Referring to FIG. 2A, it will be appreciated that event detection can be configured differently for different points of interest and mobility point combinations. It will be appreciated for example with reference to FIG. 2A that patient 190 may not be able to significantly alter the current spacing distance between the IV drip interface point of interest between feed tube 163 and patient 190 (point of interest P002) and the mobility point defined by cuff 152 of actuator assembly 1500 at location A (mobility point M001). By contrast, patient 190 has the ability to disconnect the defined IV drip using his or her right hand, accordingly it can be advantageous to carefully configure event detection for the situation where patient 190 attempts to remove feed tube 163 from patient 190 using his or her right hand. In the described scenario, event detection for the situation where patient 190 attempts to remove feed tube 163 from patient 190 using his or her right hand can be configured using the prompt window in area 520 permitting event detection configuration for the combination P002 and M002 (right hand).

Using area 530 of administrator user interface 500, administrator user can specify configuration parameters controlling actions by manager system 110 in response to an event being detected. In area 530 an administrator user can be presented with areas, e.g. areas 531, 532, and 533 allowing an administrator user to specify a response configuration parameter for each possible combination of point of interest and mobility point. Using area 530 an administrator user can specify or example configuration parameters that control or rewind speed of actuator assemblies 1500 in an unlocked mode band 151 of actuator assembly 1500 (FIG. 2B) can be relaxed to allow free movement of a patient's extremities (up to the limit imposed by the length of band 151). In some embodiments, actuator 150 can include a coil that biases band 151 so that band 151 in an unlocked mode can be wound toward actuator with tension sufficient enough to avoid sagging of the band 151 between actuator 150 and patient 190 but with tension insufficient to restrain extending of the band 151 until a limit imposed by a band length has been reached.

System 100 can be configured so that when an event is detected, e.g. a patient 190 moves a body part to a distance from a point of interest that is within a threshold distance and actuator 150 is activated to retract the patient's body part from the risk posing location. Retraction of a body part from a risk posing location can include activating actuator 150 to rewind the actuator 150 to cause roll-up of a band 151 to reduce a length of band 151 extending from actuator 150 to thereby retract the patient's body part from a risk location. Band 151 can be securely connected to related cuff 152 that is secured to a patient 190 at a body part, e.g. at a patient's hand or at an ankle located at a proximate position of a patient's foot. In addition or alternatively manager system 110 can perform retraction of a patient 190 body part by activation of a magnetic device. For example, a cuff 152 can include an active magnetic device that is activated in response to an event being detected. Manager system 110 can activate the magnetic device to cause the cuff and accordingly a body part of the patient 190 to be urged toward a magnetic coupling surface such as may be provided by a patient bed. In one embodiment, manager system 110 can activate a magnetic device as described to lock a body part in a fixed position until a timeout period has expired.

Using area 530 an administrator user can advantageously configure different combinations of points of interest and mobility points differently. In some use cases, it may be advantageous to perform a quick pullback of a body part from a risk location. In other scenarios a gently pullback may be favored. The optimal configuration in some cases can be in dependence with the patient's pathology profile and/or demographic. Using area 530 of administrator user interface 500 an administrator user can specify configuration parameters controlling a lock timeout.

System 100 can be configured so that when an event is detected, e.g. a patient 190 moves a body part to a risk position within a threshold distance of a point of interest, system 100 by activation of actuator 150 can cause retraction of the body part from that risk position. System 100 can be further configured so that when such retraction is performed, there is a lockout. That is, actuator 150 on completion of a rewind to perform a retraction can enter a locked mode, in which band 151 is restrained from being freely extended from actuator 150. Embodiments herein recognize however, that overly restrictive constraints on a patient's movement can be disadvantageous. Embodiments herein recognize that if restraints are too severe, a patient 190 can experience discomfort and stress. Accordingly, system 100 can be configured so that after an actuator 150 performs a retraction to retract band 151 and enters a lockout mode, the lockout mode can timeout some time after implementation of the lockout so that the patient 190 is once again able to freely move his or her body part to thus increase comfort and reduce stress to the patient 190.

Using area 530 an administrator user can advantageously establish different lockout timeouts for different combinations of points of interest and mobility points. It can be advantageous to differently configure lockout timeouts for different combinations of points of interest and mobility points. Also, embodiments herein recognize that optimal lock timeouts can vary in dependence, e.g. on a patient's pathology and/or demographic. Accordingly, area 530 permits free configuration of lock timeouts for different combinations of points of interest and mobility points to allow free movements of a patient's body part after an event in which a user may have caused injury to himself or herself, to relieve stress to the patient 190 and increase comfort to patient but in a way that assures the safety of the patient 190.

On completion of receiving administrator user defined configuration data at block 1101, manager system 110 can proceed to block 1102 to receive image data that can be iteratively sent from sensor system 140 at block 1401. At block 1103, manager system 110 can perform recognition processing using received image data in accordance with recognition process 113. At block 1104, manager system 110 can determine that an event has been detected, e.g. as may occur when a patient 190 moves a body part to a distance within a threshold distance.

Referring to the loop depicted by blocks 1102, 1003, and 1004 manager system 110 can perform recognition processing in accordance with recognition process 113 until a time that an event is detected at block 1104. Image data received from sensor system 140 by manager system 110 at block 1102 can be iteratively received streaming image data and recognition processing performed at block 1103 can include processing of image data on a frame by frame basis. For the performance of recognition block 1103, operation of manager system 110 can define a real-time object recognition system. Manager system 110 running recognition process 113 can include various features so that processing is performed with reduced latency, i.e. on a real-time basis. In one aspect, system 100 can be configured so that frames of image data received by manager system 110 at block 1102 from sensor system 140 are reduced size frames that exclude wherein image data external to established regions of interest of frames of data are excluded from sending by sensor system 140, e.g. in response to a control communication from manager system 110 after processing of initial frames.

Embodiments herein recognize that points of interest within patient environment 130 may be fixed or experience relatively little movement over time. According to one embodiment, system 100 can be configured so that reduced size frames having regions of interest selectively representing areas about established points of interest within patient environment 130 can be iteratively sent at block 1401. For a change in location of a point of interest as determined by recognition processing at block 1103, manager system 110 can send a control communication to sensor system 140 to update location of a region of interest so that image data, a buffer area around an encompassing an area representing a point of interest is continually sent for processing. Each region of interest should be sized for detection of a representation of an established mobility point within a defined region of interest indicative of an event wherein a patient 190 moves a mobility point into a risk location that is too close to an established point of interest. In such matter, lightweight frames can be iteratively sent for fast processing by manager system 110.

System 100 can have features to facilitate increased speed of recognition of various features including defined points of interest and mobility points. System 100 in one embodiment can include various features to improve the speed with which features such as points of interest and mobility points can be recognized by performance recognition processing at block 1103.

In one embodiment, in reference to patient environment 130 as depicted in FIG. 2A decodable indicia 142 can be formed on each mobility point which, in the example of FIG. 2A can be specified to be defined by respective cuffs 152 of actuator assemblies 1500. Decodable indicia 142 can be provided, e.g. by barcodes, glyphs, or other markings that are easy to detect by way of image data processing performed by manager system 110 at block 1103 in accordance with recognition process 113. Where system 100 uses decodable indicia 142, manager system 110 can include prepackaged decoding algorithms for efficiently decoding such decodable indicia. In one embodiment, decodable indicia 142 can be applied, e.g. with use of printed stickers that can be manually applied to each mobility point, e.g. each cuff 152. In the embodiment of FIG. 2A there is shown a single decodable indicia 142 applied to each mobility point provided by a cuff 152. However, it will be understood that for improved recognition processing, instances of decodable indicia 142 can be applied in a redundant manner throughout an entire outer surface of each mobility point and each point of interest.

Decodable indicia 142 as shown in FIG. 2A can be applied to all mobility points provided by cuff 152 and also can be formed on each point of interest, e.g. in the described example provided by interfaces associated with the defined IV drip defined by IV bag 162 and feed tube 163 and also oxygen mask 170.

With further reference to the flowchart of FIG. 4, image data processing described with reference to blocks 1401, 1102, 1103, and 1104 can include camera based spatial image data processing as set forth herein. In one embodiment spatial image data processing can be supplemented or replaced with radio signal based image data processing. Referring again to FIG. 2A.

Another aspect as set forth in FIG. 2A in one embodiment, sensor system 140 can include a plurality of proximity sensors 143 distributed at various locations throughout patient environment 130. Specifically, according to one embodiment each point of interest and each mobility point can have disposed thereon a proximity sensor 143. Each proximity sensor in one embodiment can be a battery-operated radio frequency proximity sensor. In one embodiment, each proximity sensor 143 can be in network communication with manager system 110 via network 180. Each proximity sensor 143 can include one or more radio frequency transceiver for performance of proximity detection and one or more radio transceiver for performance of network communication to facilitate bidirectional data communication with manager system 110. Each proximity sensor 143 can be configured to perform proximity detection with reference to an arbitrary surface and/or with reference to another peer proximity sensor 143. Each proximity sensor 143 can be configured to be tunable so that a threshold distance at which a flag is raised is adjustable. System 100 can be configured so that an administrator user can adjust the settings of each proximity sensor with use of administrator user interface 500, shown in FIG. 5. For example, system 100 can be configured so that an administrator user can adjust settings associated with each point of interest and mobility point pair using event configurator area 520 of administrator user interface 500, e.g. using sliding scale bars depicted in areas 521, 522, and 523 to establish distance threshold limits associated to each configured event to be detected for.

System 100 can be configured so that adjustment of a sliding scale bar as depicted, e.g. in areas 521, 522, and/or 523 adjusts a threshold triggering flag raising setting of depicted points of interest and mobility point pairs. In one embodiment, system 100 can be configured so that the sliding scale bar indicators indicated, e.g. in areas 521, 522, and 523 can be used to adjust a threshold associated with spatial image data processing as set forth herein and radio frequency proximity detection signal processing as set forth herein. In one embodiment a configuration area such as area 520 of administrator user interface 500 can be used to establish distance threshold settings associated with a single one of the exemplary described technologies of spatial image data processing and radio frequency signal image data processing.

With further reference to the flowchart of FIG. 4, manager system 110 on the positive detection of the event at block 1104 can proceed to block 1105 to perform a response to the event detected. Manager system 110 can activate event detection process 114 in the performance of response block 1105. Performing response block 1105, manager system 110 can reference a decision data structure of decision data structure area 2123 that cognitively maps detected events, e.g. a specific mobility point moving too close to a specific point of interest to actions associated with the event. The actions associated to each event can be configured in accordance with configuration parameters defined by an administrator user using area 530 of administrator user interface 500 as shown in FIG. 5.

An illustrative decision data structure that can be configured with use of administrator user defined configuration data is illustrated in Table A.

TABLE A

| Event | POI | MP | Proximity Threshold | Rewind Speed | Lock Timeout |
|---|---|---|---|---|---|
| E001 | P001 | M001 | 5 cm | 0.5 MPH | 2 Minutes |
| E002 | P002 | M002 | 10 cm | 0.8 MPH | 0.5 Minutes |
| . | . | . | . | . | . |
| . | . | . | . | . | . |
| . | . | . | . | . | . |

TABLE A-continued

| Event | POI | MP | Proximity Threshold | Rewind Speed | Lock Timeout |
|---|---|---|---|---|---|
| E00N | P00N | M00N | 4 cm | 0.0 MPH (Lock only, no rewind) | 1 Minute |
| . | . | . | . | . | . |
| . | . | . | . | . | . |
| . | . | . | . | . | . |

For performance of response according to one embodiment, manager system 110 can send an appropriate one or more control signal to a certain actuator 150 associated to an event. One or more communicated control signal can be sent with a control communication from manager system 110 to a certain actuator 150 for receipt by the actuator at block 1501. In response to receipt of the control communication at block 1501 actuator 150 can activate a retraction process at block 1502 to retract an associated band 151 in accordance with one or more control signal of the control communication, e.g. at a selected speed and at block 1502 on completion of a retraction process, actuator 150 in accordance with the one or more control signal of the control communication sent by manager system 110 at block 1105 and received by actuator 150 at block 1501 can initiate a lock timeout. During the timeout period which can be configured by an administrator user using area 530 of administrator user interface 500, the actuator 150 can restrain a patient 190 from pulling band 151 away outwardly from actuator 150. On expiration of the implemented timeout period the relevant actuator assembly 1500 can enter an unlock mode in which a patient 190 is once again free to move his or her body part in a manner so that the patient's body part is no longer restrained by band 151 (until the limit of the band length is reached). According to some configurations, it may be advantageous to merely prevent further movement of a body part toward a point of interest on the occurrence of an event rather than retract the body part from the point of interest (e.g. such action can be less frustrating to a patient 190 under some circumstances). For such control according to one embodiment, the retraction speed can be specified to be 0.0 MPH (see entry for event E00N in the depicted decision data structure of Table A).

Manager system 110 at block 1105 in addition to or alternatively to sending the one or more control communication can send an electronic notification e.g. to medical staff to alert medical staff as to the detected event which can represent a dangerous condition. The notification can be a text based notification and the content of the text based notification can be configured by an administrator user using area 530 of administrator user interface 500. In one embodiment, manager system 110 at block 1150 can send a notification to administrator client computer device 120 (which may be staffed by an administrator user who is a member of the medical staff) for display on administrator user interface 500. The notification can include e.g. a text based message specifying that a dangerous condition has occurred. The notification according to the configuration for the notification that can be defined by an administrator user using area 530 of administrator user interface 500 can have specific attributes, e.g. the text based message can specify the mobility point and the point of interest involved. In response to an event being detected, manager system 110 at block 1105 can send an electronic notification to an administrator user (who may be a member of the medical staff), the electronic notification including a text based message specifying that a dangerous condition has occurred.

At block 1106, manager system 110 can return to block 1102 to continue processing image data, e.g. one or more of spatial image data or radio frequency image data for the recognition of new events at block 1103.

Figure 6:
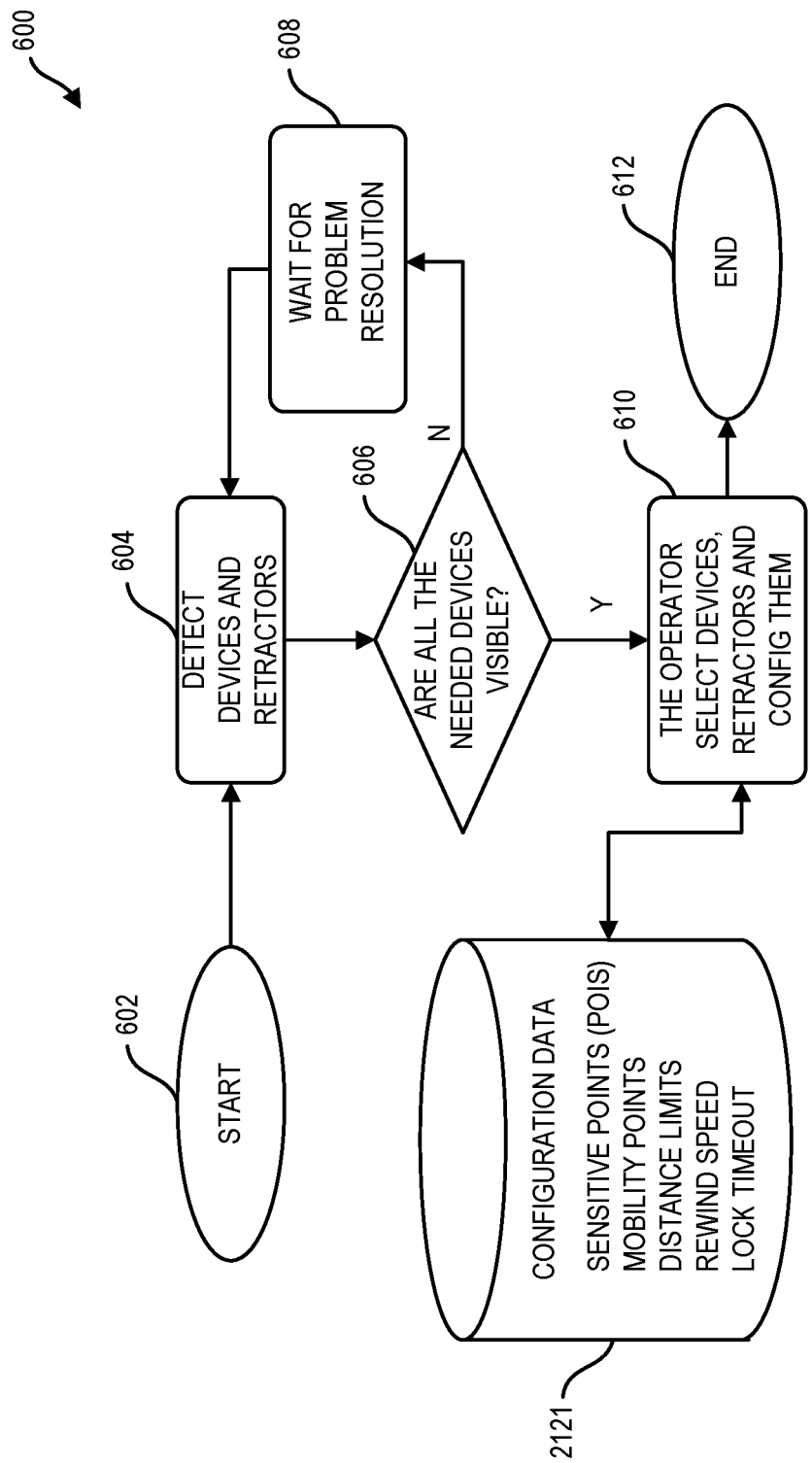
FIG. 6 is a flowchart depicting a process that can be performed by a manager system according to one embodiment.

FIG. 6 is a flowchart illustrating a process 600 that can be performed by manager system 110 in accordance with method 300 (FIG. 3) and/or the method as shown in FIG. 4. At block 602, manager system 110 can start and at block 604 can detect devices and retractors. For example, referring to administrator user interface 500 as shown in FIG. 5, manager system 110 can perform preliminary recognition processing for recognition of candidate points of interest and mobility points and can highlight such features in area 510, e.g. on a displayed still image. In addition or alternatively at block 604, manager system 110 can perform a pre-scan of radio signals emitted from any proximity sensors 143 that have been distributed into the patient environment 130 as described in connection with FIG. 2A.

At block 606, manager system 110 can determine whether all needed devices are visible, e.g. visible by processing of spatial image data and/or radio frequency image data and if not, can generate a prompt, e.g. on administrator user interface 500 prompting an administrator user to undertake corrective action. At block 608, manager system 110 can wait for resolution of a problem, e.g. which can include adjustment of a camera angle, introduction of additional cameras, adjustment of positions of radio signal proximity sensors, and the like. Manager system 110 can loop back to perform block 606 until all needed devices are visible, at which point manager system 110 can proceed to block 610 to wait for an administrator user using administrator user interface 500 to perform system configuration to configure points of interest, mobility points, events, and responses using, e.g. areas 510, 520, and 530 of administrator user interface 500.

Entered configuration parameters can be sent to configuration data area 2121 to update configuration data area 2121 of data repository 112 and the process described with reference to the flowchart of FIG. 6 can end at block 612.

Figure 7:
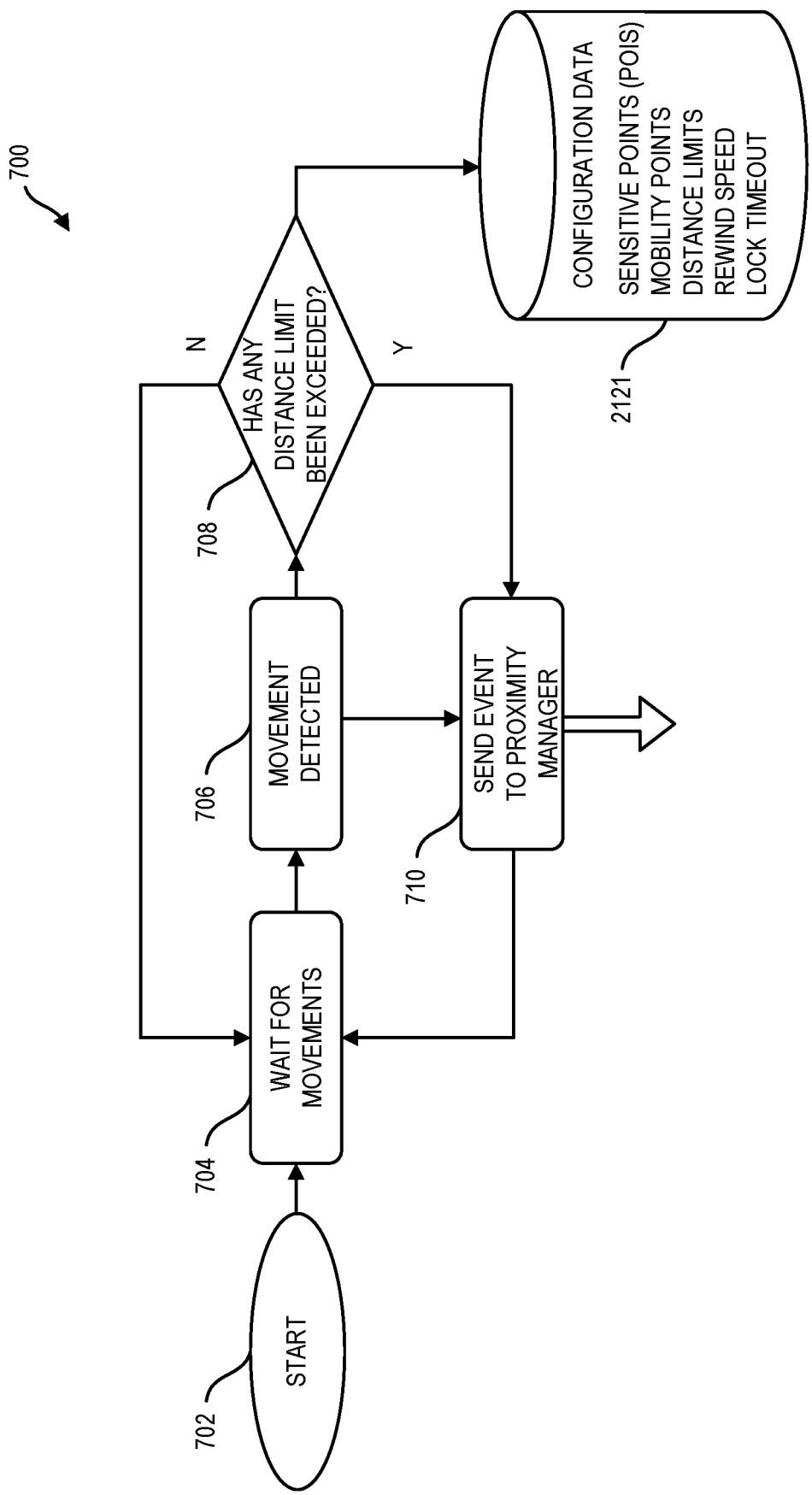
FIG. 7 is a flowchart depicting a process that can be performed by a manager system according to one embodiment.

FIG. 7 illustrates process 700 that can be performed by manager system 110 for performance of method 300 set forth in the flowchart of FIG. 3 and/or the method in reference to the flowchart of FIG. 4. At block 702 process 700 can start and at block 704 manager system 110 can wait for movement of a patient 190 to trigger an event. Block 702 of the flowchart of FIG. 7 can generally correspond to performance of block 1103 of the flowchart of FIG. 4, wherein manager system 110 performs recognition processing. At block 706, manager system 110 can perform detection of movement of a mobility point, e.g. using one or more of spatial image data and/or radio signal proximity detection image data. At block 708, manager system 110 can determine whether an event has occurred, e.g. where an event is defined by a distance between a mobility point and a point of interest being within a configured threshold distance defined by a configuration parameter.

On the determination at block 708 that a distance limit has not been exceeded, manager system 110 can return to block 704 and can iteratively perform blocks 704, 706, and 708 until a distance threshold limit has been exceeded, in which case manager system 110 can proceed to block 710 to send an event to a proximity manager. The proximity manager can be a software interface for manager system 110 that handles and responds to events. In the performance of block 708 to determine whether a distance limit has been exceeded, manager system 110 can reference configuration data, e.g. threshold distance configuration data recorded in configuration data area 2121 of data repository 112.

Figure 8:
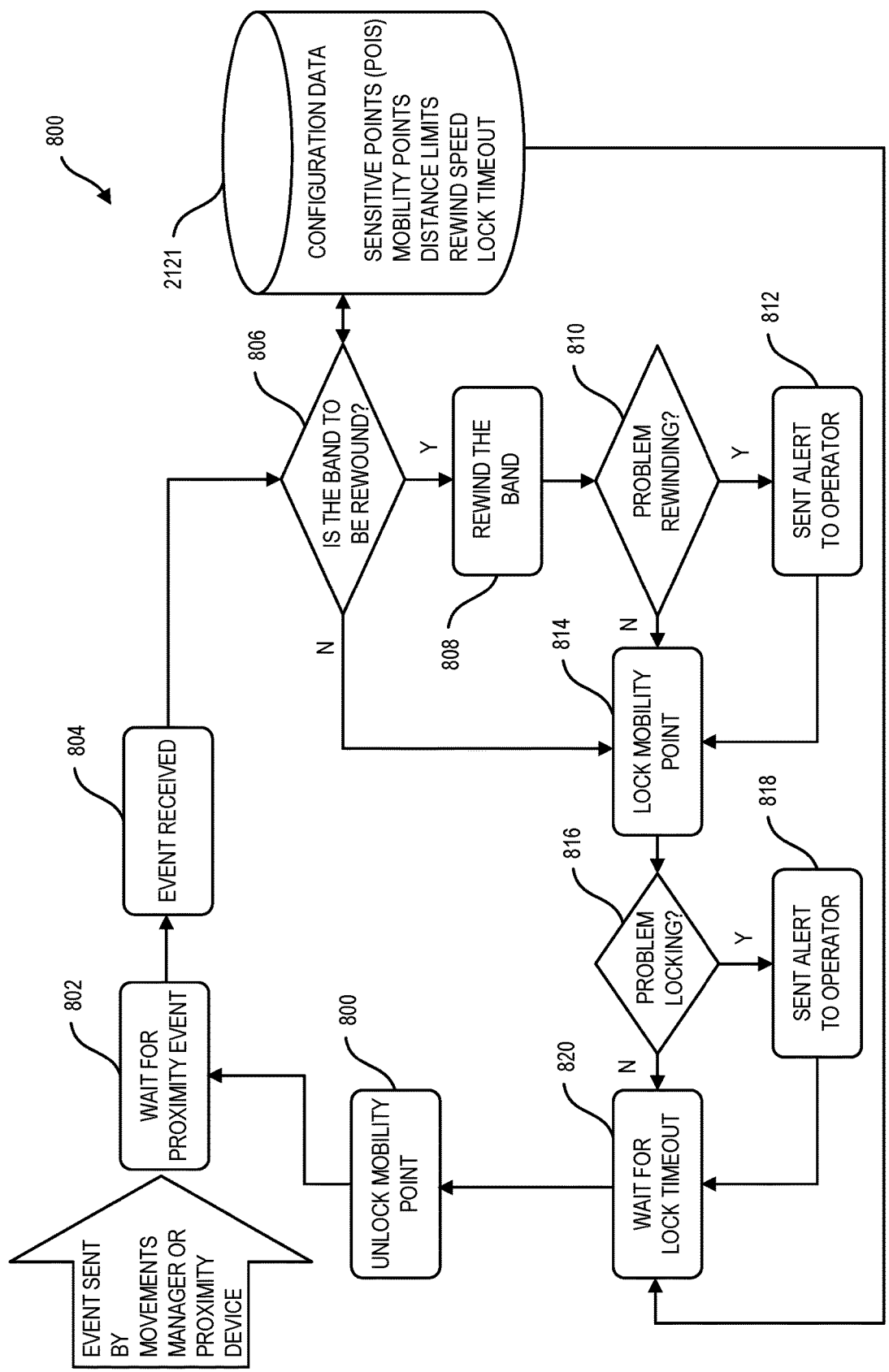
FIG. 8 is a flowchart depicting a process that can be performed by a manager system according to one embodiment.

Referring now to FIG. 8, FIG. 8 is a flowchart illustrating process 800 that can be performed by manager system 110 during performance of the method 300 as shown in FIG. 3 and/or the method depicted in the flowchart of FIG. 4 for handling of events. An event handler software interface of manager system 110 can be implements has a Daemon that waits for events. At block 802 manager system 110 can wait for a proximity event and on the occurrence of an event can proceed to block 804 to receive and process data specifying the event, e.g. the associated point of interest and mobility point. On completion of block 804, manager system 110 can proceed to block 806 to determine whether a band of an actuator assembly is to be subject to a rewind. For determining a configured action, at block 806 manager system 110 can reference configuration data of configuration data area 2121 and/or a decision data structure of data structure area 2123 of data repository 112 that cognitively maps events, e.g. points of interest and mobility points associated to actions associated to events. Each decision data structure can include data of configuration data area 2121. On the determination at block 806 that a band is to be subject to a rewind, manager system 110 can proceed to block 808 to rewind the band. Rewinding the band at block 808 can include manager system 110 sending a control communication to an actuator 150 to perform the band rewinding.

At block 810, manager system 110 can determine whether there is a problem with rewinding of the band. At block 810 manager system 110 for example, can compare an actual position of a cuff 152 by processing of image data to the position of the cuff 152 based on actuator state data. Based on a problem being determined at block 810, manager system 110 can proceed to block 812 to provide an alert to an administrator user, e.g. by display of a text based message on administrator user interface 500. Based on the determination that there is no problem with rewinding of band 151 manager system 110 can proceed to block 814 to lock mobility point.

Locking of a mobility point at block 812 can include manager system 110 sending a control communication to an appropriate actuator 150 so that band 151 of an actuator assembly 1500 is restrained from being pulled away from an actuator. Referring again to block 806, manager system 110 in some embodiments can determine on the occurrence of an event that a band does not need to be rewound. For example, a point of interest, may have moved farther away from mobility point. In the case manager system 110 at block 806 determines that a band does not need to be rewound, manager system 110 can proceed directly to block 814 to lock a mobility point without performance of blocks 808, 810, and 812. On completion of performance of locking at block 814, manager system 110 can proceed to block 816. At block 816, manager system 110 can determine whether there has been a problem with the locking, e.g. for performance of block 816 can compare an actual location of a mobility point, e.g. as defined by cuff 152 as determined by image data processing to a location of the mobility point as indicated by actuator state data of actuator 150. On the determination at block 816 that there has been a problem with locking, manager system 110 can proceed to block 818 to send an alert to an operator. For example, at block 818 manager system 110 can display a text based message indicating the alert condition on displayed administrator user interface 500 as described in reference with FIG. 5 herein. At block 820 manager system 110 can wait for a lock timeout to occur. At lock timeout can occur when a time period of a timeout has expired. Prior to a timeout expiry, manager system 110 can control actuator 150 so that actuator 150 is locked and restrains the movement of band 151 from actuator 150. On the expiration of a timeout, manager system 110 can proceed to block 822. At block 822, the relevant actuator 150 can transition from a locked mode to an unlocked mode and a patient 190 can be free to move his or her body part away from actuator 150 (the patient's extremity movement being limited only by the length of band 151). Manager system 110 on completion of block 822 can return to block 802 to wait for another proximity event.

There is set forth herein according to on embodiment a restraint member e.g. as provided by a cuff 152, structured, located and connected to be operationally connected to a body part of the patient and to provide at least some degree of constraint with respect to motion of the body part of the patient; a control circuit e.g. as provided by manager system 110; and an electric rewind device including a motor e.g. as provided by an actuator 150, the electric rewind device being structured and/or programmed respond to communications received from a control circuit by selectively operating in at least the three following modes: (i) a free mode where the electric rewind device positions the constraint member so that the patient to has at least some freedom of motion with respect to the body part, (ii) a lock mode where the electric rewind device positions the constraint member so that the patient to has substantially restricted freedom of motion with respect to the body part, and (iii) a rewind mode where the motor drives the constraint member to away from the point of interest, wherein the control circuit is programmed to perform at least the following operations: iteratively receiving movement data including information indicative of distances between the body part and one or more point of interest that should not be contacted by the body part, and iteratively determining an appropriate current mode of operation for the electric rewind device based, at least in part, upon the movement data.

There is set forth herein according to one embodiment an electric rewind device, powered by a motor, e.g. as provided by actuator 150, capable of leaving a free extension, but also of locking or rewinding a patient body part according to at least one communication received from a control unit e.g. as provided by manager system 110; the control circuit operating under control of a software program that monitors the movements of the patient by receiving input data indicating distances between the patient body part and one or more point of interest that should not be contacted by the patient body part; and the control circuit examining the received input data and sending one or more communication to the electric rewind device in response to the examining.

Some embodiments herein may include one or more of the following features, characteristics, advantages and/or operations: (i) a system to avoid dangerous movements of a patient 190 who is not completely immobilized; (ii) an electric rewind device, powered by a motor, capable of leaving a free extension, but also of locking or rewinding an arm of a patient according to requests received from a control unit; (iii) a control unit software program that monitors the movements of the patient 190 by receiving in the input the distances received from the devices placed on the "mobility points" of the patient 190 (for example, hands, feet, etc.) and points of interest that can pose risk to a patient 190 when touched (for example, needle of a drip, bandage, oxygen mask); (iv) the control unit receives data from one or more video devices, e.g. one or more camera to control the patient's global movements (e.g. if he is trying to stand up or turn); and/or (v) the control unit examining the received inputs to send one or more control communication e.g. electric commands to the electric rewind device.

A system herein can include (a) dynamic restrain bands, (b) electric apparatus for determining distances of a mobility point to a point of interest, and (c) a control unit.

Regarding (a) dynamic restrain bands herein can be fixed to a bed through an actuator provided by an electric retractor allowing the controlled extraction of the band, and locking of the band or retracting if needed. The actuator provided by an electric retractor can include a spool rotatably attached to a retractor frame. The band can be wound on the spool. In normal usage, the spool can be controlled by a coil, allowing extensions and rewinding the band when the patient 190 brings the limb back to the retractor. Depending on triggers, the retractor may lock the band extension to restrain the band from extracting from the retractor or may rewind a band by running am electric motor contained in the spool. The retractor can have a wireless apparatus to communicate with the control unit.

Regarding (b) electric apparatus can be provided for determining distances between objects such as mobility points and points of interest. In one embodiment, one or more camera can send positional inputs to the control unit of body parts with respect to fixed points (bed, room . . . ). One or more camera can include a wireless apparatus to communicate with the control unit. In one embodiment, proximity sensors can be provided to be disposed on points of interest that can be provided by sensibility points, for example an IV drip, or the oxygen mask, that has to be preserved, and mobility points, for example the hands, the legs, that has to be left free as general condition. If a configured distance limit is exceeded a proximity event can occur. Proximity sensors can have a wireless apparatus to communicate with the control unit.

Regarding (c) a control unit e.g. as provided by manager system 110 can manage proximity events detected using one or more camera or sent by proximity sensors, manage movements data from video devices, and trigger retractor actions. Components of a system can be configured by applications executed on computers or mobile devices. In the configuration phase, the control unit can detect the visible devices and using the application an administrator can set the points of interest and mobility points to be used. Distance limits can be established between points, for example, the right hand of the patient 190 has to be at not less than 5 cm from an IV drip but for the left arm, the patient's left arm should not be at more than one meter from a bed of the patient 190. A list of actions to put in place for any distance limit reached, for example lock a band, rewind a band and/or alarm the medical staff. A control unit can implement a timeout for a locking mechanism that locks the band so that the band can be extended again from an actuator after a timeout. The application can prompt an administrator user to define a configuration for a system based on type of patient 190 and the pathology. An administrator user the can change the configuration to adapt it to specific needs.

Embodiments herein can include monitoring software that is able to recognize the dangerous movements for a patient 190 for example movement which may result e.g. in disengagement from an IV drip, or an oxygen mask.

In one embodiment control communications can be activated in response to an event to cause mechanical movement of a body part of a patient 190 e.g. an extremity. In one embodiment, mechanical movement can be urged with use of a retractable band as set forth herein. In another embodiment, mechanical movement can be urged with use of one or more activatable magnetic device activated with use of electrical signals.

Some magnetic devices can be activated only when these movements are recognized. For example a first magnetic device can be provided in a wrist cuff and a second magnetic device can be provided on a bed of patient 190 and in response to a detected event the magnetic devices can be activated to lock the movement of the hands and in some cases activate an alarm for the medical staff.

Once a patient 190 becomes quiet, the locking mechanism can be deactivated. Monitoring software can be provided that uses one or more camera device depending on the kind of movement it has to find. It can also use signals output by proximity sensors disposed in defined points of interest and mobility points.

Software can be provided to distinguish between allowed and not allowed movements, and to react immediately with temporary restraint, avoiding the use of permanent restraint.

Embodiments herein can include monitoring a patient 190 in a bed recovering in a hospital, wherein there are provided some devices e.g. electrical devices such as one or more camera and/or proximity sensor monitoring the movements of the patient 190. Monitoring software can take in input the data passed by a movements detector device e.g. camera and/or proximity sensor, and can be configured by administrator user defined configuration parameters.

Configuration parameters can include e.g. points of interest e.g. "sensibility points" that can be provided for example an IV drip, or the oxygen mask, that should remain untouched by a patient 190 to assure proper operation.

Configuration parameters can include mobility points for example. Some "mobility points" for example can include the hands, the legs, that are to be left to allow free movement as a general condition.

Configuration parameters can include defined events which defined events can include defined threshold distance parameters. Some distance limits between points of interest and mobility points, can, for example include that the right hand of the patient 190 has to be at not less than 5 cm from an IV drip, but for the left arm, the patient's left arm should not be at more than one meter from the bed.

Configuration parameters can include defined one or more action in response to a detected event. A list of actions to put in place for any distance limit reached, for example can include e.g. retracting a band, activating a magnetic device to move a patient 190 body part and/or alarm the medical staff and/or to establish a timeout for a locking mechanism.

Parameters can be configurable basing on type of patient 190 and pathology. Monitoring software can be run as a daemon that waits to receive some movement changes from a sensor system.

As soon as a change occurs, a monitoring system can check to determine whether the distance between the mobility point and the corresponding point of interest (according with the configuration), until it reaches the limit. At this point the monitoring software can react as configured, for example locking an actuator, retracting a band and or activating a magnetic field to restrain the movement of the hand. After a configurable timeout is reached, a locking mechanism can be deactivated to "free" again the patient 190.

Dangerous movements for the patient 190 can be avoided, but without completely immobilizing the patient 190. A patient's limbs may not be firmly tied to the bed, but rather a patient 190 can be comfortably tethered using an extensible band of variable length. The band length can be controlled by an electric rewind, powered by a motor, capable of leaving a free extension, but also of locking or rewinding according to requests received from a control unit.

A control unit can be programmed with monitoring software that monitors the movements of the patient 190 by receiving in the input the distances received from the devices placed on the 'mobility points' of the patient 190 (hands, feet . . . ) and points of interest that should not be touched (e.g. needle of an IV drip, bandage, oxygen mask). The control unit can also receive data from a camera to control the patient's global movements (e.g. if the patient 190 is trying to stand up or turn). Monitoring software can be engaged to distinguish between allowed and not allowed movements to react immediately with a temporary restraint. Dynamic restraints can be used to limit patient 190 movements. Embodiments herein facilitate substantial and safe movement of a patient 190 reducing the frustrations to a patient 190 often in critical conditions.

In one embodiment software managing the control can include a proximity event manager and the movements manager. If one or more camera and/or proximity sensor outputs data indicating that a distance with a point of interest has been exceeded, a proximity event can be triggered. The movements manager can continuously analyze global movement reported by one or more camera. The proximity event manager can receive events and reacts as configured, triggering e.g. a retractor of an actuator to rewind and lock the bands, and or activation of one or more magnetic device to restrain a patient 190. The proximity event manager can send alerts to operators. After the configurable timeout is reached, a lock can be deactivated to "free" again the patient 190.

Certain embodiments herein may offer various technical computing advantages involving computing advantages to address problems arising in the realm of computer networks. Embodiments herein can feature for example event handling event detection that uses one or more imaging technology. Image data processed by event detection processes herein can include for example, spatial image data and/or radio signal image data. Embodiments herein can feature use of one or more decision data structure such as a decision data structure that cognitively maps events to one or more actions associated with such events so that actions can be differentiated based on attributes of an event that has been detected. Embodiments herein can feature lightweight data processing such as lightweight image data processing that utilizes, e.g. regions of interests to reduce frame size of image data frames subject to processing. Embodiments herein can include use of image data processing that incorporates training data and machine learning. Embodiments herein can feature configuration platform that permits an administrator user to enter a range control of configuration parameters controlling such aspects as points of interest to be recognized, mobility points to be recognized, events to be detected for, and responses to be initiated in response to particular events. High speed data processing methodologies that can be employed can also include use of training images to train a recognition processor to identify select features more rapidly and also use of decodable indicia dataforms. Some embodiments herein can employ multiple technologies for recognition of features and detection of events, e.g. in some embodiments both spatial image data processing and radio signal image data processing can be performed. Sensor systems employed in some embodiments can include multiple sensors such as multiple camera sensors, multiple proximity sensors, or a combination of camera and proximity sensors. Embodiments herein can feature processing of history data respecting past configurations and past performance of a recognition system for more efficient and accurate operation.

Figure 9:
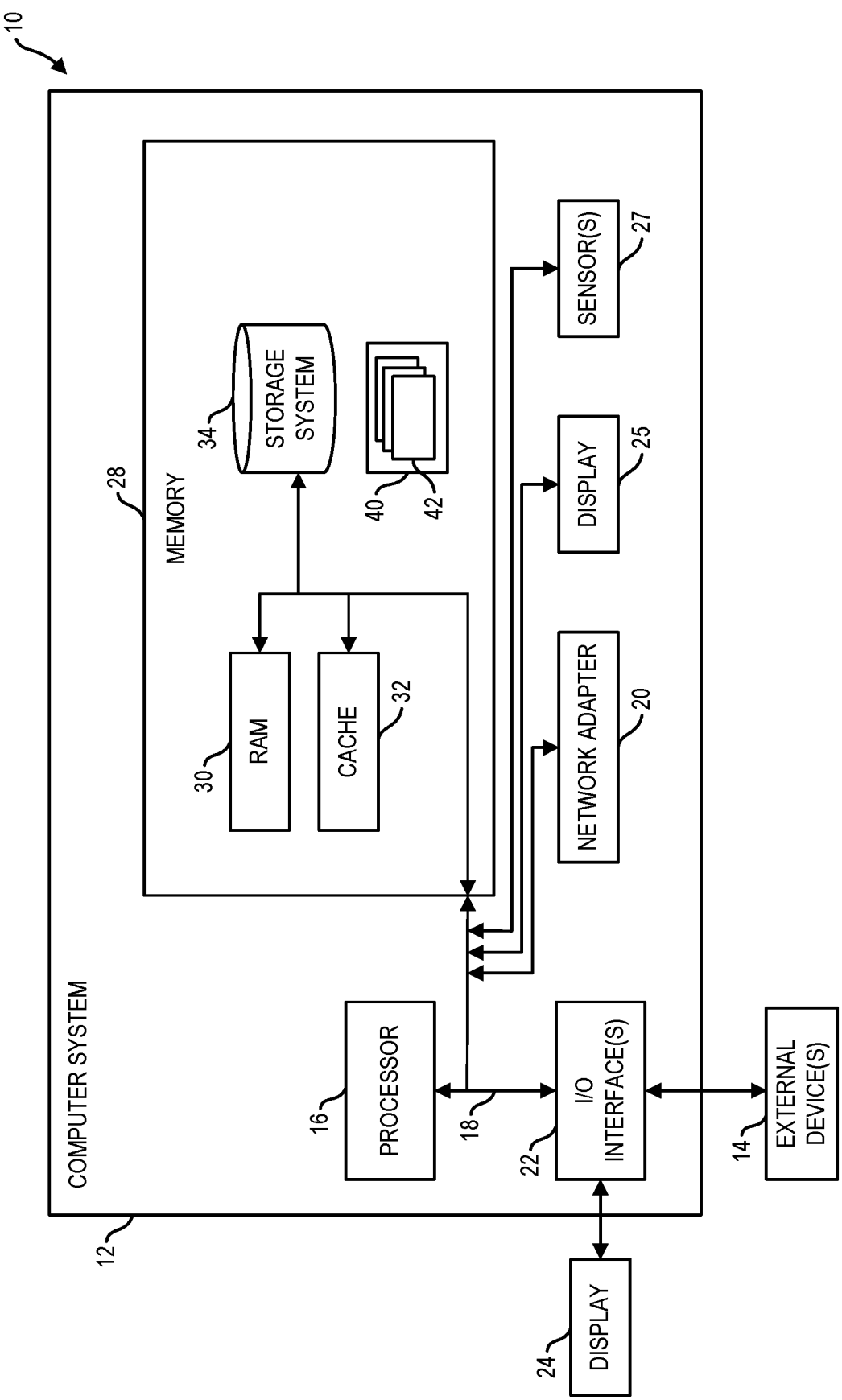
FIG. 9 depicts a computing node according to one embodiment.
Figure 10:
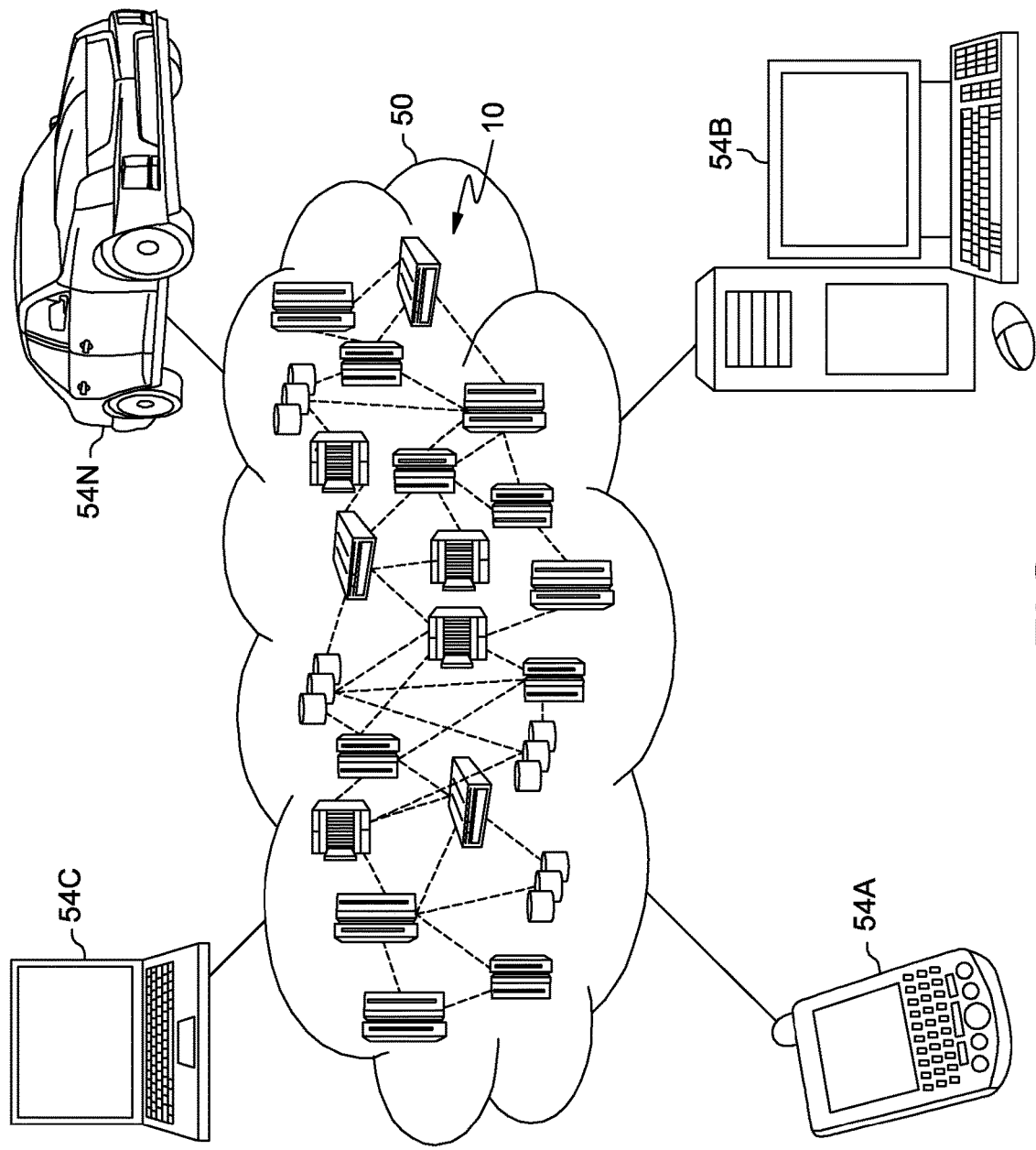
FIG. 10 depicts a cloud computing environment according to one embodiment.
Figure 11:
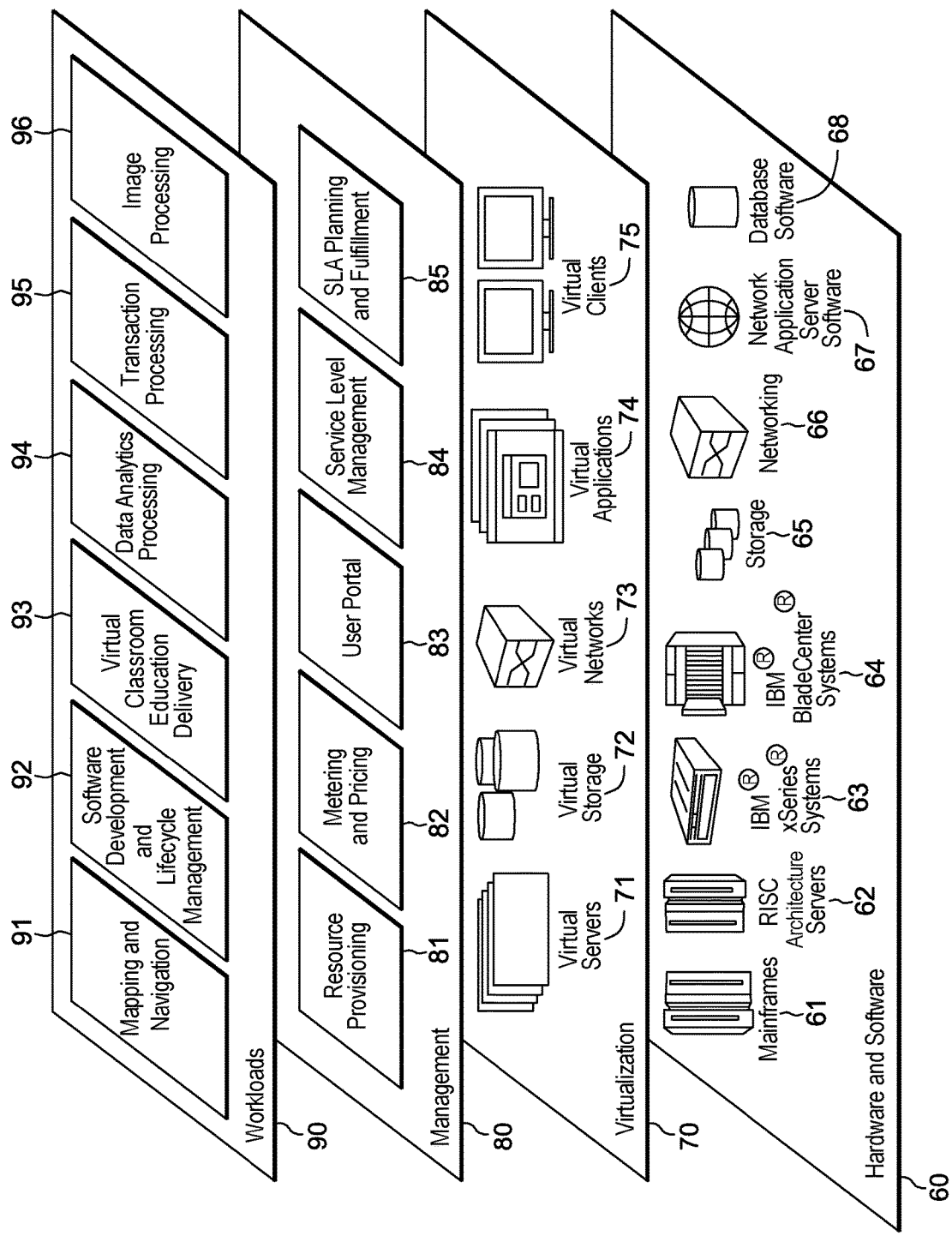
FIG. 11 depicts abstraction model layers according to one embodiment.

FIGS. 9-11 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 9, a schematic of an example of a computing node is shown. Computing node 10 is only one example of a computing node suitable for use as a cloud computing node and is not intended to suggest any limitation as to the scope of use or functionality of embodiments of the invention described herein. Regardless, computing node 10 is capable of being implemented and/or performing any of the functionality set forth hereinabove. Computing node 10 can be implemented as a cloud computing node in a cloud computing environment, or can be implemented as a computing node in a computing environment other than a cloud computing environment.

In computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system.

Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 9, computer system 12 in computing node 10 is shown in the form of a computing device. The components of computer system 12 may include, but are not limited to, one or more processor 16, a system memory 28, and a bus 18 that couples various system components including system memory 28 to processor 16. In one embodiment, computing node 10 is a computing node of a non-cloud computing environment. In one embodiment, computing node 10 is a computing node of a cloud computing environment as set forth herein in connection with FIGS. 10-11.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. One or more program 40 including program processes 42 can generally carry out the functions set forth herein. One or more program 40 including program processes 42 can define machine logic to carry out the functions set forth herein. In one embodiment, manager system 110 can include one or more computing node 10 and can include one or more program 40 for performing functions described with reference to method 300 of FIG. 3 and functions described with reference to manager system 110 as set forth in the flowchart of FIG. 4. In one embodiment, administrator client computer device 120 can include one or more computing node 10 and can include one or more program 40 for performing functions described with reference to administrator client computer device 120 as set forth in the flowchart of FIG. 4. In one embodiment, sensor system 140 can include one or more computing node 10 and can include one or more program 40 for performing functions described with reference to sensor system 140 as set forth in the flowchart of FIG. 4. In one embodiment, actuator 150 can include one or more computing node 10 and can include one or more program 40 for performing functions described with reference to actuator 140 as set forth in the flowchart of FIG. 4. In one embodiment, the computing node based systems and devices depicted in FIG. 1 can include one or more program for performing function described with reference to such computing node based systems and devices.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc. In addition to or in place of having external devices 14 and display 24, which can be configured to provide user interface functionality, computing node 10 in one embodiment can include display 25 connected to bus 18. In one embodiment, display 25 can be configured as a touch screen display and can be configured to provide user interface functionality, e.g. can facilitate virtual keyboard functionality and input of total data. Computer system 12 in one embodiment can also include one or more sensor device 27 connected to bus 18. One or more sensor device 27 can alternatively be connected through I/O interface(s) 22. One or more sensor device 27 can include a Global Positioning Sensor (GPS) device in one embodiment and can be configured to provide a location of computing node 10. In one embodiment, one or more sensor device 27 can alternatively or in addition include, e.g., one or more of a camera, a gyroscope, a temperature sensor, a humidity sensor, a pulse sensor, a blood pressure (bp) sensor or an audio input device. Computer system 12 can include one or more network adapter 20. In FIG. 10 computing node 10 is described as being implemented in a cloud computing environment and accordingly is referred to as a cloud computing node in the context of FIG. 10.

Referring now to FIG. 10, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 10 and cloud computing environment 50 can communicate with any type of computerized device over any type of network and/or network addressable connection (e.g., using a web browser).

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components 96 for recognizing objects and detecting events such as proximity events as set forth herein. The processing components 96 can be implemented with use of one or more program 40 described in FIG. 9.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have"

(and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Forms of the term "based on" herein encompass relationships where an element is partially based on as well as relationships where an element is entirely based on. Methods, products and systems described as having a certain number of elements can be practiced with less than or greater than the certain number of elements. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A system to avoid dangerous movements of a human patient who is not completely immobilized, said system comprising:
    a restraint member configured to be operationally connected to a hand or foot body part of the human patient and to provide at least some degree of constraint with respect to motion of the hand or foot body part of the human patient;
    an electric rewind device, powered by a motor configured for leaving a free extension, but also of locking or rewinding the human patient hand or foot body part according to at least one communication received from a control circuit, wherein the electric rewind device is structured and/or programmed to respond to communications received from the control circuit by selectively operating in at least the three following modes: (i) a free mode where the electric rewind device positions the restraint member so that the human patient has at least some freedom of motion with respect to the hand or foot body part, (ii) a lock mode where the electric rewind device positions the restraint member so that the human patient has substantially restricted freedom of motion with respect to the body part, and (iii) a rewind mode where the motor drives the restraint member away from one or more point of interest, wherein the control circuit is programmed to perform at least the following operations: (a) iteratively receiving movement data including information indicative of distances between the body part and the one or more point of interest that should not be contacted by the body part, and (b) iteratively determining an appropriate current mode of operation for the electric rewind device based, at least in part, upon the movement data;
    the control circuit operating under control of a software program that monitors movements of the human patient by receiving input data indicating distances between the human patient hand or foot body part and the one or more point of interest that should not be contacted by the human patient hand or foot body part; and
    the control circuit examining the received input data and sending one or more communication to the electric rewind device in response to the examining, wherein a user interface displays an image representation of the human patient hand or foot body part and permits an administrator to select the image representation of the human patient hand or foot body part to designate the human patient hand or foot body part as a point to be subject to relative distance monitoring with respect to the one or more point of interest, wherein the system is configured by the administrator specifying a first action to move the restraint member away from a first point of interest at a first speed responsively to determining that a first portion of the human patient's body defined by the human patient hand or foot body part is within a distance threshold of a first point of interest, and wherein the system is configured by the administrator specifying a second action to move a second restraint member worn on a second portion of the human patient's body away from a second point of interest at a second speed responsively to determining that the second portion of the human patient's body is within a threshold distance of the second point of interest, and wherein the second speed is different from the first speed.

2. The system of claim 1, wherein the user interface displays an image representation of the human patient's body and permits the administrator to selectively designate a portion of the image representation of the human patient's body to selectively designate a portion of the human patient's body as a point to be subject to relative distance monitoring with respect to the one or more point of interest, wherein the user interface displays an image representation of medical equipment apparatus and permits the administrator to selectively designate a portion of the image representation of medical equipment apparatus to selectively designate a portion of the human patient's medical equipment apparatus as a point to be subject to relative distance monitoring by the control circuit, wherein the system subjects the first portion of the human patient's body defined by the human patient hand or foot body part and the first point of interest to first relative distance monitoring, and subjects the second portion of the human patient's body and the second point of interest to second relative distance monitoring, wherein the user interface permits the administrator to specify the first action by the system in response to the first relative distance monitoring, and wherein the user interface permits the administrator to specify the second action by the system in response to the second relative distance monitoring, wherein the restraint member is worn on the first portion of the human patient's body.

3. A system to avoid dangerous movements of a human patient who is not completely immobilized, said system comprising:
    a restraint member configured to be operationally connected to a hand or foot body part of the human patient and to provide at least some degree of constraint with respect to motion of the hand or foot body part of the human patient;

an electric rewind device, powered by a motor, configured for leaving a free extension, but also of locking or rewinding the human patient hand or foot body part according to at least one communication received from a control circuit, wherein the electric rewind device is structured and/or programmed to respond to communications received from the control circuit by selectively operating in at least the three following modes: (i) a free mode where the electric rewind device positions the restraint member so that the human patient has at least some freedom of motion with respect to the hand or foot body part, (ii) a lock mode where the electric rewind device positions the restraint member so that the human patient has substantially restricted freedom of motion with respect to the hand or foot body part, and (iii) a rewind mode where the motor drives the restraint member away from one or more point of interest, wherein the control circuit is programmed to perform at least the following operations: (a) iteratively receiving movement data including information indicative of distances between the hand or foot body part and the one or more point of interest that should not be contacted by the hand or foot body part, and (b) iteratively determining an appropriate current mode of operation for the electric rewind device based, at least in part, upon the movement data;

the control circuit operating under control of a software program that monitors movements of the human patient by receiving input data indicating distances between the human patient hand or foot body part and the one or more point of interest that should not be contacted by the human patient hand or foot body part; and the control circuit examining the received input data and sending one or more communication to the electric rewind device in response to the examining, wherein a user interface displays an image representation of the human patient hand or foot body part and permits an administrator to select the image representation of the human patient hand or foot body part to designate the human patient hand or foot body part as a point to be subject to relative distance monitoring with respect to the one or more point of interest, wherein the system in response to the sending of the one or more communication performs establishing a lock timeout, the lock timeout being a time period for which the human patient is restrained from moving the hand or foot body part toward the point of interest.

4. The system of claim 3, wherein the system in response to the sending of the one or more communication further performs each of: (A) retracting the hand or foot body part away from the point of interest; (B) establishing a speed for retracting the hand or foot body part away from the point of interest; (C) locking the hand or foot body part to restrain movement of the body part toward the point of interest.

5. A system to avoid dangerous movements of a human patient who is not completely immobilized, said system comprising:

a restraint member configured to be operationally connected to a hand or foot body part of the human patient and to provide at least some degree of constraint with respect to motion of the hand or foot body part of the human patient;

an electric rewind device, powered by a motor, configured for leaving a free extension, but also of locking or rewinding the human patient hand or foot body part according to at least one communication received from a control circuit, wherein the electric rewind device is structured and/or programmed to respond to communications received from the control circuit by selectively operating in at least the three following modes: (i) a free mode where the electric rewind device positions the restraint member so that the human patient has at least some freedom of motion with respect to the hand or foot body part, (ii) a lock mode where the electric rewind device positions the restraint member so that the human patient has substantially restricted freedom of motion with respect to the body part, and (iii) a rewind mode where the motor drives the restraint member away from one or more point of interest, wherein the control circuit is programmed to perform at least the following operations: (a) iteratively receiving movement data including information indicative of distances between the hand or foot body part and the one or more point of interest that should not be contacted by the hand or foot body part, and (b) iteratively determining an appropriate current mode of operation for the electric rewind device based, at least in part, upon the movement data;

the control circuit operating under control of a software program that monitors movements of the human patient by receiving input data indicating distances between the human patient hand or foot body part and the one or more point of interest that should not be contacted by the human patient hand or foot body part; and the control circuit examining the received input data and sending one or more communication to the electric rewind device in response to the examining, wherein a user interface displays an image representation of the human patient hand or foot body part and permits an administrator to select the image representation of the human patient hand or foot body part to designate the human patient hand or foot body part as a point to be subject to relative distance monitoring with respect to the one or more point of interest, wherein the system in response to the sending of the one or more communication performs locking the electric rewind device so that the human patient is restrained by the restraint member from moving the hand or foot body part toward the point of interest until a configured timeout period has expired.

6. The system of claim 5, wherein the hand or foot body part is a hand, wherein the one or more point of interest is a point on an IV drip, and wherein system in response to the sending of the one or more communication further performs retracting the hand away from the point on the IV drip, the electric rewind device having the restraint member fitted on the patient's wrist, wherein the restraint member is provided by a cuff.

* * * * *